US011026669B2

(12) United States Patent
Castelli et al.

(10) Patent No.: US 11,026,669 B2
(45) Date of Patent: Jun. 8, 2021

(54) COLLAPSIBLE DILATOR

(71) Applicant: Medtronic Vascular, Inc., Santa Rosa, CA (US)

(72) Inventors: Brian Castelli, Rohnert Park, CA (US); Michael Krivoruchko, Forestville, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 427 days.

(21) Appl. No.: 15/648,512

(22) Filed: Jul. 13, 2017

(65) Prior Publication Data

US 2019/0015088 A1 Jan. 17, 2019

(51) Int. Cl.
*A61B 17/02* (2006.01)
*A61B 17/34* (2006.01)
(Continued)

(52) U.S. Cl.
CPC .............. *A61B 17/02* (2013.01); *A61B 17/22* (2013.01); *A61B 17/34* (2013.01);
(Continued)

(58) Field of Classification Search
CPC ..... A61B 17/3417; A61B 17/34; A61B 17/02; A61B 17/3439; A61B 17/3431; A61M 29/00; A61M 2025/0687; A61M 25/0074; A61M 2025/0098; A61M 2025/0025; A61M 2025/0024
See application file for complete search history.

(56) References Cited

U.S. PATENT DOCUMENTS 2,201,749 A * 5/1940 Vandegrift ............ A61M 29/02
27/24.2
3,030,953 A * 4/1962 Koehn ............... A61B 17/3415
604/166.01
(Continued)

FOREIGN PATENT DOCUMENTS

EP 0334116 A1 9/1989
WO 2008024883 A1 2/2008

OTHER PUBLICATIONS

International Search Report and Written Opinion of International Application No. PCT/US2018/041459, dated Sep. 18, 2018, 13 pp.

*Primary Examiner* — David W Bates
(74) *Attorney, Agent, or Firm* — Dicke, Billig & Czaja, PLLC

(57) ABSTRACT

In some examples, an introducer apparatus includes an outer elongated member defining a lumen extending therethrough, the lumen having a lumen dimension in cross-section, and a dilator configured to be received within the lumen of the outer elongated member, the dilator may comprise a proximal section, a distal section comprising a distal end of the dilator, and an intermediate section disposed between the proximal section and the tapered distal section. In some examples, the intermediate section may define a through-opening that configures the intermediate section to be collapsible from an expanded configuration to a collapsed configuration. In the collapsed configuration, the intermediate section may have a first dilator dimension in cross-section that is less than a second dilator dimension in cross-section when the intermediate section is in the expanded configuration.

30 Claims, 12 Drawing Sheets

(51) Int. Cl.
 *A61M 25/06* (2006.01)
 *A61B 17/22* (2006.01)
 *A61M 29/00* (2006.01)

(52) U.S. Cl.
 CPC ......... *A61B 17/3417* (2013.01); *A61M 29/00* (2013.01); *A61M 25/0662* (2013.01)

(56) References Cited

U.S. PATENT DOCUMENTS

| | | | | |
|---|---|---|---|---|
| 3,082,769 A * | 3/1963 | Palmer | A61M 5/3286 | 604/166.01 |
| 3,199,398 A * | 8/1965 | Weisz | F16B 13/005 | 411/80.1 |
| 3,388,703 A * | 6/1968 | Bowes | A61M 25/065 | 604/166.01 |
| 3,612,050 A * | 10/1971 | Sheridan | A61M 25/0606 | 604/166.01 |
| 3,703,898 A * | 11/1972 | Zackheim | A61D 1/02 | 604/105 |
| 4,281,658 A * | 8/1981 | Child | A61M 29/00 | 119/14.19 |
| 4,406,656 A * | 9/1983 | Hattier | A61M 25/0009 | 604/103.14 |
| 4,408,938 A * | 10/1983 | Maguire | F16B 13/126 | 411/181 |
| 4,668,221 A * | 5/1987 | Luther | A61M 25/0606 | 604/164.03 |
| 4,716,901 A * | 1/1988 | Jackson | A61B 17/3439 | 128/200.26 |
| 4,760,843 A * | 8/1988 | Fischer | A61B 17/686 | 411/178 |
| 4,850,975 A * | 7/1989 | Furukawa | A61M 25/0662 | 604/170.01 |
| 4,921,479 A * | 5/1990 | Grayzel | A61M 25/0668 | 604/160 |
| 5,011,478 A * | 4/1991 | Cope | A61M 25/0662 | 604/165.02 |
| 5,201,756 A * | 4/1993 | Horzewski | A61M 25/0023 | 604/104 |
| 5,292,311 A * | 3/1994 | Cope | A61M 25/0662 | 604/165.02 |
| 5,295,994 A * | 3/1994 | Bonutti | A61B 17/0218 | 604/103 |
| 5,304,119 A * | 4/1994 | Balaban | A61M 37/0069 | 604/107 |
| 5,454,365 A * | 10/1995 | Bonutti | A61B 17/0218 | 600/204 |
| 5,499,975 A * | 3/1996 | Cope | A61M 25/0662 | 604/164.1 |
| 5,618,272 A * | 4/1997 | Nomura | A61M 25/0606 | 604/161 |
| 5,713,904 A * | 2/1998 | Errico | A61B 17/686 | 606/327 |
| 5,851,207 A * | 12/1998 | Cesarone | A61B 17/1728 | 606/86 B |
| 5,904,685 A * | 5/1999 | Walawalkar | A61F 2/0805 | 606/104 |
| 6,033,359 A * | 3/2000 | Doi | A61B 5/1076 | 600/104 |
| 6,120,480 A * | 9/2000 | Zhang | A61M 25/0662 | 604/164.01 |
| 6,293,743 B1 * | 9/2001 | Ernst | F16B 13/066 | 411/24 |
| 6,436,119 B1 | 8/2002 | Erb et al. | | |
| 6,579,264 B1 * | 6/2003 | Rossi | A61M 25/0662 | 604/164.05 |
| 6,726,699 B1 * | 4/2004 | Wright | A61B 17/3421 | 606/185 |
| 7,094,218 B2 * | 8/2006 | Rome | A61M 25/0028 | 604/256 |
| 7,766,920 B2 * | 8/2010 | Ciccone | A61B 17/1615 | 606/104 |
| 7,803,142 B2 * | 9/2010 | Longson | A61M 25/065 | 604/158 |
| 8,226,716 B2 * | 7/2012 | Mckernan | A61B 17/1714 | 623/13.17 |
| 8,398,696 B2 * | 3/2013 | Buiser | A61B 17/1215 | 623/1.11 |
| 8,636,784 B2 * | 1/2014 | Greenhalgh | A61B 17/864 | 606/313 |
| 9,101,373 B2 * | 8/2015 | Norton | A61B 17/1796 | |
| 9,114,227 B2 * | 8/2015 | Blanchard | A61B 17/3415 | |
| 9,161,794 B2 * | 10/2015 | Garvey | A61B 17/8685 | |
| 10,405,890 B2 * | 9/2019 | Ratron | A61B 17/8685 | |
| 10,413,287 B2 * | 9/2019 | Heiges | A61B 1/32 | |
| 2005/0059934 A1 * | 3/2005 | Wenchell | A61B 17/3439 | 604/167.01 |
| 2005/0277946 A1 * | 12/2005 | Greenhalgh | A61B 17/3421 | 606/108 |
| 2006/0116690 A1 * | 6/2006 | Pagano | A61B 17/025 | 606/93 |
| 2007/0010716 A1 * | 1/2007 | Malandain | A61B 90/35 | 600/224 |
| 2008/0097332 A1 * | 4/2008 | Greenhalgh | A61B 17/3421 | 604/167.06 |
| 2008/0183220 A1 * | 7/2008 | Glazer | A61B 17/686 | 606/303 |
| 2008/0200943 A1 * | 8/2008 | Barker | A61B 17/3439 | 606/192 |
| 2009/0192552 A1 * | 7/2009 | Andersen | A61B 17/7032 | 606/302 |
| 2009/0281580 A1 * | 11/2009 | Emannuel | A61B 17/8625 | 606/304 |
| 2009/0306586 A1 * | 12/2009 | Ross | A61B 17/3439 | 604/93.01 |
| 2010/0042164 A1 * | 2/2010 | Lee | A61B 17/686 | 606/304 |
| 2010/0217090 A1 * | 8/2010 | Heiges | A61B 17/02 | 600/217 |
| 2010/0249785 A1 * | 9/2010 | Betts | A61B 17/1617 | 606/79 |
| 2012/0022575 A1 * | 1/2012 | Mire | A61B 5/4893 | 606/198 |
| 2012/0179102 A1 * | 7/2012 | Blanchard | A61B 17/3415 | 604/164.1 |
| 2013/0184736 A1 | 7/2013 | Aman et al. | | |
| 2014/0142394 A1 * | 5/2014 | Cataltepe | A61M 25/0102 | 600/208 |
| 2016/0074067 A1 * | 3/2016 | Furnish | A61B 17/3439 | 606/108 |
| 2016/0310166 A1 * | 10/2016 | Eaton | A61M 25/0074 | |
| 2017/0128086 A1 * | 5/2017 | Slobitker | A61B 17/1617 | |
| 2017/0252062 A1 * | 9/2017 | Fitterer | A61B 17/3423 | |

* cited by examiner

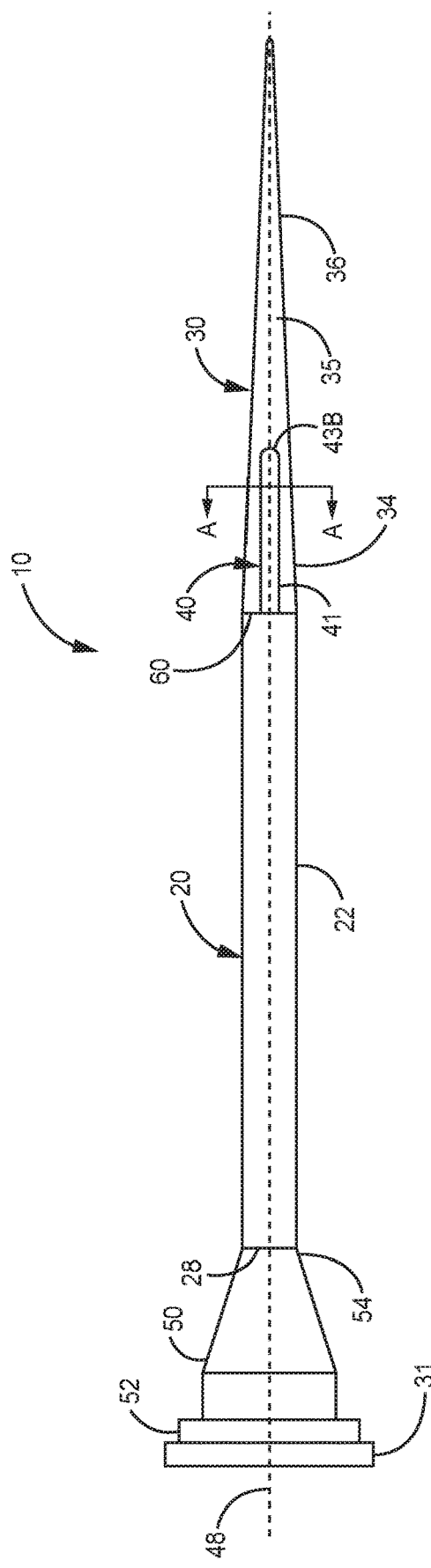

COLLAPSIBLE DILATOR

TECHNICAL FIELD

The disclosure relates to a medical dilator.

BACKGROUND

Introducer apparatuses may be used to percutaneously access tissue of a patient, e.g., vasculature of a patient, to aid the insertion of catheters or other medical devices into vasculature or other tissue site. Such apparatuses may be used in medical procedures such as angiography, angioplasty, and others. In some examples, an introducer apparatus may include a sheath defining a lumen, and a dilator received within the lumen of the sheath and extending past a distal end of the sheath. During some medical procedures, a clinician may puncture a blood vessel with a needle or a similar device, and the introducer apparatus may be subsequently advanced through the puncture site in the blood vessel. As the introducer apparatus is advanced through the puncture site, the dilator, which may be at a leading end of the introducer apparatus, progressively dilates an insertion path to the puncture site, as well as the puncture site, which may facilitate the advancement of the sheath through the insertion path and through the puncture site. After the sheath is introduced through the blood vessel wall through the puncture site, the dilator may be removed from the sheath, and the sheath may be used to introducer one or more other medical devices into the blood vessel.

SUMMARY

This disclosure describes example dilators that can be used, for example, to facilitate access to the vasculature of a patient. The disclosure also describes example introducer apparatuses that include an outer elongated member defining a lumen, and a dilator configured to be received within the lumen of the outer elongated member. In some examples, a dilator defines a through-opening that configures the dilator to be collapsible from an expanded configuration to a collapsed configuration, which may facilitate withdrawal of the dilator proximally through an outer elongated member. For example, a dilator may comprise a proximal section, a distal section, and an intermediate section disposed between the proximal section and the distal section, where the intermediate section defines at least one through-opening that configures the intermediate section to be collapsible from an expanded configuration to a collapsed configuration. When the intermediate section is in the collapsed configuration, it may be withdrawn through the lumen of an outer elongated member. Also described herein are methods of using the dilator and introducer apparatus, as well as methods of making the dilator and introducer apparatus.

Clause 1: In one example, a device includes a dilator configured to be received within a lumen of an outer elongated member, the dilator comprising a proximal section and an intermediate section defining a through-opening that configures the intermediate section to be collapsible from an expanded configuration to a collapsed configuration.

Clause 2: In some examples of the device of clause 1, the dilator further includes a distal section comprising a distal end of the dilator, the intermediate section being disposed between the proximal section and the distal section.

Clause 3: In some examples of the device of clause 2, the distal section of the dilator is tapered toward the distal end of the dilator.

Clause 4: In some examples of the device of any of clauses 1-3, in the collapsed configuration, the intermediate section has a first dilator dimension measured in a direction orthogonal to a longitudinal axis of the dilator, and in the expanded configuration, the intermediate section has a second dilator dimension measured in the direction, the second dilator dimension being greater than the first dilator dimension.

Clause 5: In some examples of the device of clause 4, the through-opening extends along about 5% to about 50% of a perimeter of a cross-section of the dilator taken orthogonal to a longitudinal axis of the dilator.

Clause 6: In some examples of the device of any of clauses 1-5, the through-opening includes two or more through-openings.

Clause 7: In some examples of the device of clause 6, at least two of the two or more through-openings are positioned on opposite sides of a central longitudinal axis of the dilator.

Clause 8: In some examples of the device of clause 6 or 7, the two or more through-openings are longitudinally spaced from one another relative to a longitudinal axis of the dilator.

Clause 9: In some examples of the device of any of clauses 1-8, the through-opening is centered along a central longitudinal axis of the dilator.

Clause 10: In some examples of the device of any of clauses 1-8, the through-opening is off-center relative from a central longitudinal axis of the dilator.

Clause 11: In some examples of the device of any of clauses 1-10, the dilator defines a dilator lumen configured to receive a guidewire, the through-opening extending through the dilator lumen.

Clause 12: In some examples of the device of clause 11, the through-opening bisects the dilator lumen into a first portion and a second portion, the device further including an inner elongated member extending between the first and second portions of the dilator lumen.

Clause 13: In some examples of the device of clause 12, the inner elongated member is exposed by the through-opening.

Clause 14: In some examples of the device of clause 12 or 13, the inner elongated member extends only partially through the dilator.

Clause 15: In some examples of the device of clause 12 or 13, the inner elongated member extends from the proximal section of the dilator to a distal section of the dilator.

Clause 16: In some examples of the device of any of clauses 12-15, the dilator is overmolded around the inner elongated member.

Clause 17: In some examples of the device of any of clauses 12-16, the inner elongated member comprises a hypotube.

Clause 18: In some examples of the device of any of clauses 1-17, the dilator defines a dilator lumen configured to receive a guidewire, the through-opening extending around the dilator lumen.

Clause 19: In another example, an apparatus includes an outer elongated member defining a lumen extending therethrough, the lumen having a lumen dimension in cross-section, a dilator configured to be received within the lumen of the outer elongated member, the dilator including a proximal section and an intermediate section defining a through-opening that configures the intermediate section to be collapsible from an expanded configuration to a collapsed configuration where in the collapsed configuration, the intermediate section has a dilator dimension in cross-section that is less than or equal to the lumen dimension.

Clause 20: In some examples of the apparatus of clause 19, the dilator further includes a distal section comprising a distal end of the dilator, the intermediate section being disposed between the proximal section and the distal section.

Clause 21: In some examples of the apparatus of clause 20, the distal section of the dilator is tapered toward a distal end of the dilator.

Clause 22: In some examples of the apparatus of clause 20 or 21, when the proximal section of the dilator is positioned in the lumen of the outer elongated member and the intermediate section is in the expanded configuration, the intermediate section and the distal section extend distally past a distal end of the outer elongated member.

Clause 23: In some examples of the apparatus of any of clauses 20-22, the proximal section and the distal section of the dilator each have outer dimensions in cross-section less than or equal to the lumen dimension.

Clause 24: In some examples of the apparatus of any of clauses 20-23, the lumen of the outer elongated member includes a first lumen and the dilator defines a second lumen configured to receive a guidewire.

Clause 25: In some examples of the apparatus of clause 24, the second lumen extends around the through-opening.

Clause 26: In some examples of the apparatus of clause 24, the second lumen extends through the through-opening.

Clause 27: In some examples of the apparatus of clause 24 or 26, the through-opening bisects the second lumen into a first portion and a second portion, the apparatus further including an inner elongated member extending between the first and second portions of the second lumen.

Clause 28: In some examples of the apparatus of clause 27, the inner elongated member is exposed by the through-opening.

Clause 29: In some examples of the apparatus of clause 27 or 28, the inner elongated member extends only partially through the dilator.

Clause 30: In some examples of the apparatus of clause 27 or 28, the inner elongated member extends from the proximal section of the dilator to the distal section of the dilator.

Clause 31: In some examples of the apparatus of any of clauses 27-30, the dilator is overmolded around the inner elongated member.

Clause 32: In some examples of the apparatus of any of clauses 27-31, the inner elongated member includes a hypotube.

Clause 33: In some examples of the apparatus of any of clauses 27-32, the apparatus further includes a guidewire configured to be received within an inner lumen of the inner elongated member.

Clause 34: In some examples of the apparatus of any of clauses 19-33, when the proximal section of the dilator is positioned in the lumen of the outer elongated member and the intermediate section is in the expanded configuration and extends distally past a distal end of the outer elongated member, the outer elongated member and the intermediate section have substantially same outer dimensions.

Clause 35: In some examples of the apparatus of any of clauses 19-34, the dilator dimension is substantially equal to the lumen dimension.

Clause 36: In some examples of the apparatus of any of clauses 19-35, the dilator dimension is a first dilator dimension, and in the expanded configuration, the intermediate section has a second dilator dimension in cross-section, the second dilator dimension being substantially equal to the lumen dimension.

Clause 37: In some examples of the apparatus of any of clauses 19-36, the dilator dimension is a first dilator dimension, and in the expanded configuration, the intermediate section has a second dilator dimension in cross-section, the second dilator dimension being greater than the lumen dimension.

Clause 38: In some examples of the apparatus of any of clauses 19-37, the dilator dimension is a first dilator dimension, and in the expanded configuration, the intermediate section has a second dilator dimension in cross-section, the second dilator dimension being greater than an outer dimension of the outer elongated member.

Clause 39: In some examples of the apparatus of any of clauses 19-38, the dilator dimension is a first dilator dimension, and in the expanded configuration, the intermediate section has a second dilator dimension in cross-section, the second dilator dimension being substantially equal to an outer dimension of the outer elongated member.

Clause 40: In some examples of the apparatus of any of clauses 19-39, the through-opening extends along about 5% to about 50% of a perimeter of a cross-section of the dilator taken orthogonal to a longitudinal axis of the dilator.

Clause 41: In some examples of the apparatus of any of clauses 19-40, the through-opening comprises two or more through-openings.

Clause 42: In some examples of the apparatus of clause 41, at least two of the two or more through-openings are positioned on opposite sides of a central longitudinal axis of the dilator.

Clause 43: In some examples of the apparatus of clause 41 or 42, the two or more through-openings are longitudinally spaced from one another relative to a longitudinal axis of the dilator.

Clause 44: In some examples of the apparatus of any of clauses 19-43, the through-opening is off-center from a central longitudinal axis of the dilator.

Clause 45: In some examples of the apparatus of any of clauses 19-43, the through-opening is centered along a central longitudinal axis of the dilator.

Clause 46: In some examples of the apparatus of any of clauses 19-45, the dilator is configured to be withdrawn proximally into the lumen of the outer elongated member when the intermediate section of the dilator is in the collapsed configuration.

Clause 47: In some examples of the apparatus of any of clauses 19-46, the lumen dimension includes a first lumen dimension and a second lumen dimension, the second lumen dimension being less than the first lumen dimension, a distalmost portion of the lumen having the first lumen dimension, and the lumen of the outer elongated member tapers from the first lumen dimension to the second lumen dimension to facilitate withdrawal of the intermediate section of the dilator in a proximal direction into the lumen.

Clause 48: In some examples of the apparatus of any of clauses 19-47, the outer elongated member defines a substantially continuous outer diameter.

Clause 49: In another example, a method includes introducing a medical device into a tissue of a patient, the medical device including an outer elongated member defining a lumen extending therethrough, the lumen having a lumen dimension in cross-section, and a dilator configured to be received within the lumen of the outer elongated member, the dilator including a proximal section, and an intermediate section defining a through-opening that configures the intermediate section to be collapsible from an expanded configuration to a collapsed configuration, advancing the medical device through the tissue of the patient with the proximal section of the dilator within the lumen of the outer elongated member and the intermediate section of the dilator in the expanded configuration and extending distally past a distal end of the outer elongated member, and withdrawing the intermediate section of the dilator proximally into the lumen of the outer elongated member to cause the intermediate section to assume the collapsed configuration within the lumen.

Clause 50: In some examples of the method of clause 49, the dilator further includes a distal section comprising a distal end of the dilator, the intermediate section being disposed between the proximal section and the distal section.

Clause 51: In some examples of the method of clause 49 or 50, in the collapsed configuration, the intermediate section has a dilator dimension in cross-section that is less than or equal to the lumen dimension.

Clause 52: In some examples of the method of any of clauses 49-51, when the proximal section of the dilator is positioned in the lumen of the outer elongated member and the intermediate section is in the expanded configuration and extends distally past a distal end of the outer elongated member, the outer elongated member and the intermediate section have substantially same outer dimensions.

Clause 53: In some examples of the method of any of clauses 49-52, the through-opening extends along about 5% to about 50% of a perimeter of a cross-section of the dilator taken orthogonal to a longitudinal axis of the dilator.

Clause 54: In some examples of the method of any of clauses 49-53, the through-opening comprises two or more through-openings.

Clause 55: In some examples of the method of any of clauses 49-54, the lumen of the outer elongated member comprises a first lumen and the dilator defines a second lumen, the method further comprising introducing a guidewire into the first and second lumens.

Clause 56: In some examples of the method of clause 55, the second lumen extends around the through-opening, and introducing the guidewire into the second lumen comprises introducing the guidewire into the second lumen around the through-opening.

Clause 57: In some examples of the method of clause 55, the second lumen extends through the through-opening, and wherein introducing the guidewire into the second lumen comprises introducing the guidewire through the through-opening.

Clause 58: In some examples of the method of clause 55 or 57, the through-opening bisects the second lumen into a first portion and a second portion, the medical device further including an inner elongated member extending between the first and second portions of the second lumen, the method further comprising introducing the guidewire into the inner elongated member.

Clause 59: In some examples of the method of clause 58, the inner elongated member is exposed by the through-opening.

Clause 60: In some examples of the method of any of clauses 49-59, the lumen dimension includes a first lumen dimension and a second lumen dimension that is less than the first lumen dimension, a distalmost portion of the lumen having the first lumen dimension, and the lumen of the outer elongated member tapers from the first lumen dimension to the second lumen dimension to facilitate withdrawal of the intermediate section of the dilator in a proximal direction into the lumen.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 1 is a perspective view of an example introducer apparatus including an outer elongated member and a collapsible dilator received within a lumen of the outer elongated member, where an intermediate section of the dilator is in an expanded configuration and extends distally past a distal end of the outer elongated member.

Figure 2A:
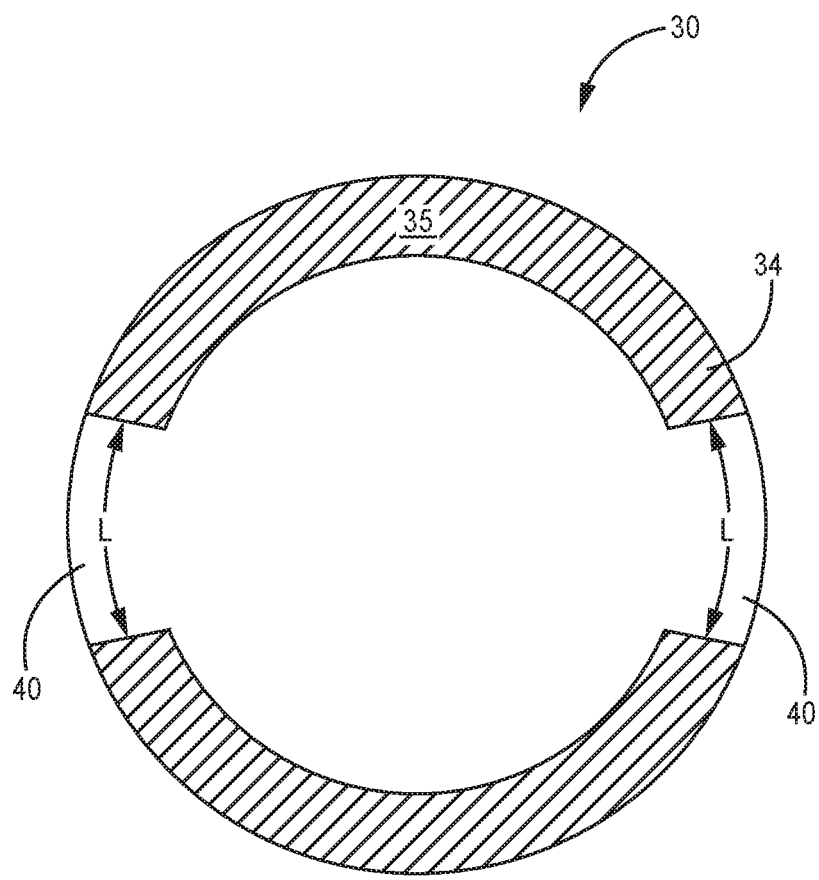
FIG. 2A is a cross-sectional view of the dilator of FIG. 1 in an expanded configuration, where the cross-section is taken along a plane orthogonal to a longitudinal axis of the dilator.

The details of one or more examples of this disclosure are set forth in the accompanying drawings and the description below. Other features, objects, and advantages of this disclosure will be apparent from the description and drawings, and from the claims.

DETAILED DESCRIPTION

An introducer apparatus can be used during a medical procedure to access a tissue site, such as a site within vasculature of a patient, a subcutaneous tissue site, or another tissue site. For example, an introducer apparatus can be used to establish percutaneous access to a blood vessel to facilitate introduction of a catheter or another medical device into the blood vessel during a vascular procedure. Example vasculature procedures include, but are not limited to, vascular surgery, endovascular treatment of vessels, or other procedures during which one or more medical devices may be introduced into the vasculature.

In some examples described herein, an introducer apparatus includes an outer elongated member, such as a sheath, and a collapsible dilator configured to be received within a lumen of the outer elongated member and proximally withdrawn through the lumen of the outer elongated member. The collapsible dilator defines one or more through-openings configured to allow at least a portion of dilator to collapse from an expanded configuration to a lower profile collapsed configuration, which may facilitate withdrawal of the dilator proximally through the lumen of the outer elongated member.

During a vascular procedure, a clinician may create an insertion path from an entry point accessible from outside a patient to a target site within the vasculature, such as with a needle or similar device. Once an insertion path has been created, the clinician may introduce an introducer apparatus into the insertion path from the outside of the patient to the target site, thereby enlarging the insertion path to an outer dimension of the introducer apparatus. The clinician then may withdraw the dilator proximally through the outer elongated member, leaving the outer elongated member in place within the insertion path. Subsequent medical devices may then be introduced into the body of the patient, e.g., delivered to a treatment site, through the outer elongated member without requiring the clinician to remove the outer elongated member and insert a separate introducer catheter. However, in other examples, a separate introducer catheter may be used in addition to or instead of the outer elongated member of the introducer apparatus. In addition, in other examples, a clinician may use the introducer apparatus to create the insertion path instead of using a needle or other separate device.

Some introducer apparatuses may include an outer elongated member and a dilator that have different outer diameters at a junction where the two components meet. For example, in order to allow the dilator to be proximally withdrawn into a lumen of the outer elongated member, the dilator may have a smaller outer diameter than the outer elongated member. The different outer diameters may define a raised edge (e.g., a ridge or similar formation) at an outer junction of an outer elongated member and a dilator. During introduction of such an apparatus, the raised edge may contact a portion of the patient tissue, which may cause abrasion or other adverse impacts to tissue of a patient as the apparatus is pushed distally through the tissue. In addition, when such a raised edge contacts the patient tissue, such as at a portion of the vasculature, the resulting increase in resistance also may cause a tip of the outer elongated member to become bent or peeled back. Bending or peeling back of a tip of an introducer sheath may cause further abrasion to the tissue.

In examples described herein, an introducer apparatus includes a collapsible dilator, which may allow at least a section of the dilator to have a larger outer dimension (e.g., an outer diameter) than a dimension (e.g., a diameter) of a lumen of an outer elongated member, while still permitting the dilator to be proximally withdrawn into the lumen of the outer elongated member. Because at least a section of the dilator has a larger outer dimension than an inner lumen of the outer elongated member, any edge defined at an outer junction of the sheath and the dilator may be reduced compared to a dilator that has an outer dimension along its entire length that is equal to the dimension of the inner lumen of the outer elongated member. In some examples, the outer elongated member and at least a section of the dilator may have substantially same outer dimensions at the transition region between the two components when the dilator is received within the outer elongated member, such that there is substantially no edge (e.g., no edge or an edge that is small enough to have a minimal impact on tissue of a patient). However, in other examples, the outer elongated member and at least a section of the dilator may have different outer dimensions at the transition region between the two components when the dilator is received within the outer elongated member.

A collapsible dilator that has a larger outer dimension than an inner lumen of an outer elongated member may help define smooth transition region between the dilator and the outer elongated member on the outer surface of the introducer apparatus when the apparatus is in an assembled configuration. This may be due to the reduction or even elimination of a raised edge between the outer elongated member and the dilator when the dilator is inserted inside the lumen of the outer elongated member. The smooth transition region between dilator and outer elongated member may reduce any adverse interference or resistance between the introducer apparatus and patient tissue during introduction of the introducer apparatus into the patient. In addition, the collapsible dilator may help reduce the potential for components of the introducer apparatus to inadvertently change shape during use, e.g., by reducing or even eliminating a raised edge between the sheath and dilator that may cause a tip of the sheath to become bent or peeled back during use.

During some medical procedures, such as a vascular procedure, one or more medical devices may be delivered through a catheter or sheath after a dilator has been used to enlarge the insertion path extending from the exterior of a patient's body to a puncture site in a wall of a vessel. In some examples of introducer apparatuses described herein, a collapsible dilator, in an expanded state, defines an outer dimension that is greater than the dimension of an inner lumen of an outer elongated member. In such examples, the collapsibility of the dilator may allow the dilator to assume a smaller outer dimension and, therefore, may allow the dilator to be withdrawn through the inner lumen of the outer elongated member. Thus, the outer elongated member may be left in place within the insertion path and a clinician may introduce medical devices through the inner lumen of the outer elongated member after withdrawal of the dilator.

In contrast to introducer apparatuses in which a sheath and dilator are non-separably joined such that the entire apparatus (both outer elongated member and dilator) must be removed from the patient before another medical device may be introduced through the insertion path, an introducer apparatus that is configured such that the dilator can be withdrawn proximally through the lumen of the outer elongated member may allow for a more efficient vascular procedure. It some cases, may be desirable to minimize the number of devices that are introduced into a patient in order to simplify the medical procedure and, in some cases, shorten the amount of time required to perform the medical procedure. In this way, the introducer apparatuses described herein may help facilitate the simplification of a medical procedure.

In some example methods of using an introducer apparatus described herein, the introducer apparatus that includes an outer elongated member and a collapsible dilator may be introduced into a tissue of a patient, such as into a portion of a vasculature of a patient. The introducer apparatus may then be advanced through the tissue of the patient, with the dilator received within the lumen of the outer elongated member and the distal end of the dilator extending past a distal end of the outer elongated member. A clinician may apply a proximal pulling force to the dilator, thereby causing at least part of the dilator extending past the distal end of the outer elongated member to assume a collapsed configuration having a cross-sectional dimension that is less than or equal to a cross-sectional dimension of the lumen of the outer elongated member. With the dilator in the collapsed configuration, the dilator may be withdrawn proximally into the lumen of the outer elongated member and removed from the introducer apparatus while the outer elongated member remains positioned in the insertion path.

The length, outer dimensions, and other characteristics of the dilators and outer elongated members described herein may be selected based on one or more factors, such as the medical procedure with which the introducer apparatus may be used, the anatomical characteristics of the vasculature or other tissue into which the apparatus is to be introduced, the medical devices that may be introduced into the patient using the introducer apparatus, and the like. Although the outer dimensions are primarily referred to as outer diameters herein, in other examples, the components of the introducer apparatus, including the dilator and the outer elongated member, may have any suitable cross-sectional shape, where the cross-section is taken in a direction orthogonal to a longitudinal axis of the respective component.

While a vasculature of a patient is primarily referred to herein, the devices, apparatuses, and techniques described herein can be used to access other tissue sites in a patient. For example, an example introducer apparatus described herein can be used to enlarge a space within subcutaneous tissue, such as during a procedure to place an electrical stimulation lead, electrical stimulation device, or other device within non-vasculature tissue. Thus, descriptions of the use of the devices, apparatuses, and techniques described herein should not be interpreted as being limited to procedures involving portions of a patient's vasculature.

FIG. 1 is a side view of an example introducer apparatus 10, which includes outer elongated member 20 and collapsible dilator 30. In the example shown in FIG. 1, outer elongated member 20 and dilator 30 are assembled, such that dilator 30 extends through an inner lumen 24 defined by outer elongated member 20. As discussed in further detail below, dilator 30 is configured to collapse from an expanded configuration to a collapsed configuration. In the expanded configuration, at least a portion of dilator 30 that extends past a distal end of outer elongated member 20 (when outer elongated member 20 and dilator 30 are assembled) has an outer diameter that is greater than the diameter of lumen 24 (and, therefore, greater than inner diameter of outer elongated member 20). In the collapsed configuration, at least the portion of dilator 30 that extends past the distal end of outer elongated member 20 has an outer diameter less than or equal to the diameter of lumen 24, such that dilator 30 may be withdrawn proximally through lumen 24 when dilator 30 is in the collapsed configuration.

Introducer apparatus 10 of FIG. 1 can be used with any suitable medical procedure, such as a vascular procedure. In some examples, a medical procedure may include the introduction of an atherectomy device for disrupting an atherosclerotic plaque. In other examples, a medical procedure may include the introduction of a device for stenting or otherwise reinforcing a portion of a body vessel at a treatment site. In still other examples, a medical procedure may include the introduction of a device for delivery or withdrawal of a fluid, such as the delivery of a radiopaque or pharmacological fluid, or the withdrawal of blood from within a vessel.

Outer elongated member 20 defines inner lumen 24 (shown in FIG. 6), which extends from proximal end 28 to distal end 26. When introducer apparatus 10 is assembled, dilator 30 is received within inner lumen 24 of outer elongated member 20, and extends distally past distal end 26 of outer elongated member 20. Outer elongated member 20 includes housing member 50 mechanically connected to or integrally formed with proximal end 28 of outer elongated member 20. In some examples, housing member 50 includes proximal end 52 and distal end 54.

Introducer apparatus 10 has sufficient rigidity to permit introducer apparatus 10 to be introduced through tissue of a patient without buckling. In addition, dilator 30 may have sufficient rigidity to permit dilator 30 to dilate tissue to expand an insertion path through tissue of the patient as dilator 30 is inserted through the insertion path. The components of introducer apparatus 10 may be formed from any suitable biocompatible materials. In some examples, one or both of outer elongated member 20 and dilator 30 may be formed from a suitably polymer, such as, but not limited to polytetrafluoroethylene (PTFE), a polyether block amide (e.g., PEBAX), polyurethane, polyethylene, vinyl, expanded-polytetrafluoroethylene (ePTFE), or other polymers. In addition, or instead, one or both of outer elongated member 20 and dilator 30 may include one or more other materials, such as a biocompatible metal. In other examples, one or more components of introducer apparatus 10 may include a material that may be visualized during fluoroscopy, such as a nickel-titanium alloy (e.g., Nitinol), or another suitable radiopaque material.

In some examples, proximal end 52 of housing member 50 may include a threaded member, a Luer-type fitting, or another coupling feature which may permit a clinician to couple housing member 50 to a handle or other device designed to allow the clinician to grasp the proximal end of introducer apparatus 10. In some examples, housing member 50 may be an integral portion of outer elongated member 20. In other examples, housing member 50 may be removable from proximal end 28 of outer elongated member 20. In such examples, distal end 54 of housing member 50 may include a threaded member, a Luer-type fitting, or other coupling feature which may permit housing member 50 to be releasably coupled to outer elongated member 20, thereby providing interchangeability of housing member 50 with other devices. Housing 50 may define a lumen or channel (not shown) extending from proximal end 52 to distal end 54. The channel extending through housing 50 has a dimension in cross-section that is equal to or greater than a cross-sectional dimension of lumen 24 of outer elongated member 20. Thus, dilator 30, or another device which may be inserted or withdrawn through lumen 20, may also pass through the channel of housing 50.

In some examples, dilator 30 may include handle 31 at a proximal end of dilator 30, which provides a structure that a clinician may use to grasp dilator 30, e.g., to withdraw dilator 30 from outer elongated member 20. In some cases, it may be desirable to secure outer elongated member 20 and dilator 30 together in the assembled state, e.g., for ease of use. Thus, in some examples, handle 31 and housing 50 may be configured to engage together to help secure elongated member 20 and dilator 30 to each other in the longitudinal direction (along longitudinal axis 48) or in a rotational direction (about longitudinal axis 48), or both. For example, handle 31 and housing 50 may be threadably connected to fix the relative longitudinal position between elongated member 20 and dilator 30. As another example, handle 31 and housing 50 may include complementary mating features (e.g., projections/protrusions) that engage to fix the relative longitudinal position and/or rotational position of elongated member 20 and dilator 30. Longitudinal axis 48 may be, for example, a central longitudinal axis of outer elongated member 20, dilator 30, or both.

Dilator 30 includes proximal section 32 (labeled in FIG. 3), intermediate section 34, and distal section 36, wherein intermediate section 34 is positioned between proximal section 32 and distal section 36. In some examples, intermediate section 34 and distal section 36 have substantially the same (e.g., the same or nearly the same) lengths (measured in a longitudinal direction). In other examples, distal section 36 may be longer than intermediate section 34 or intermediate section 34 may be longer than distal section 36. The relative lengths of intermediate proximal section 32, intermediate section 34, and distal section 36 may be selected based on, for example, the length of the insertion path through tissue that is dilated using introducer apparatus 10. Intermediate section 34 and/or distal section 34 may be elongated to accommodate longer insertion paths.

When introducer apparatus 10 is assembled in the insertion configuration shown in FIG. 1, proximal section 32 of dilator 30 is received fully within inner lumen 24 of outer elongated member 20, at least a portion of intermediate section 34 extends distally past distal end 26 of outer elongated member 20, and the entirety of distal section 36 extends distally past distal end 26 of outer elongated member 20. In the example shown in FIG. 1, intermediate section 34 and distal section 36 are each tapered in a distal direction to facilitate advancement of dilator 30 through tissue. In some examples, distal section 36 may have a sharp cutting tip or point to further aid the advancement of dilator 30 through tissue. Due to the tapered configuration of intermediate section 34 and distal section 36, a cross-sectional dimension of a proximal portion of intermediate section 34 and a proximal portion of distal section 36 is greater than a cross-sectional dimension of a distal portion of the respective sections 34, 36, where the cross-sections are taken in a direction orthogonal to longitudinal axis 48. The degree of the taper of intermediate section 34 and distal section 36 may vary depending upon the medical procedure and treatment site at which introducer apparatus 10 may be used. For example, the angle formed by the slope of the outer wall of distal section 36 and longitudinal axis 48 may be approximately 45°, although other angles may be formed in other examples. In other examples, only a portion of intermediate section 34 or only distal section 36 of dilator 30 may be tapered.

In the assembled, insertion configuration of FIG. 1, intermediate section 34 of dilator 30 extends distally from within a distal portion of inner lumen 24. In some examples, as shown in FIG. 1, intermediate section 34 defines through-opening 40, which extends through a width of dilator 30, where the width is measured in a direction orthogonal to longitudinal axis 48. In examples in which through-opening 40 is positioned at a tapered portion of intermediate section 34, the width of dilator 30 may be measured at any point of intermediate section 34 that includes through-opening 40. As described below in further detail, through-opening 40 allows intermediate section 34 to compress (e.g., radially inward) into the collapsed configuration, thereby allowing a clinician to withdraw dilator 30 proximally through inner lumen 24 of outer elongated member 20. In the examples described below, through-opening 40 may have any suitable dimensions that allow intermediate section 34 to become sufficiently compressed upon exertion of a proximal pulling force upon proximal section 32 of dilator 30. The compression force on intermediate section 34 may be applied by outer elongated member 20, e.g., by an inner wall of outer elongated member 20, as a clinician pulls proximally on dilator 30.

In the example shown in FIG. 1, through-opening 40 extends longitudinally from a proximal portion of intermediate section 34 to a more distal portion of intermediate section 34, and extends radially through intermediate section 34 in a substantially orthogonal (e.g., orthogonal or nearly orthogonal) orientation to a longitudinal axis 48. For example, through-opening may extend through a sidewall of intermediate section 34 of dilator 30, where the sidewall extends along a longitudinal axis 48 and structurally defines an outer surface of dilator 30.

Through-opening 40 enables intermediate section 34 to be collapsible from an expanded configuration to a collapsed configuration. When intermediate section 34 is in the expanded configuration, as illustrated in FIG. 1, at least a portion of intermediate section 34 has an outer diameter that is greater than a diameter of inner lumen 24 of outer elongated member 20. For example, in the example shown in FIG. 1, elongated outer member 20 and intermediate section 34 have substantially the same outer dimensions at the outer location 60 (which may be a junction between member 20 and dilator 30), as discussed in greater detail below with respect to FIG. 5. When a clinician applies a proximal pulling force to a proximal end of dilator 30, as may be done during a medical procedure, the proximal pulling force causes intermediate section 34 to collapse radially inward and assume a collapsed configuration in which a cross-sectional dimension of intermediate section 34 is less than or equal to a cross-sectional dimension of inner lumen 24. Thus, when intermediate section 34 is in the collapsed configuration, intermediate section 34 has an outer diameter that is less than or equal to the diameter of inner lumen 24, such that dilator 30 may be withdrawn proximally through lumen 24 and removed from introducer apparatus 10.

Through-opening 40 may, in some examples, be located along intermediate section 34 such that the entirety of through-opening 40 is distal to distal end 26 of outer elongated member 20 when dilator 30 is fully inserted in outer elongated member 20 (e.g., such that handle 31 and housing 50 are touching). In other examples, through-opening 40 may be located along intermediate section 34 such that at least a portion of through-opening 40 is within inner lumen 24 of outer elongated member 20 (or, in other words, when a portion of through-opening 40 is proximal to distal end 26) when dilator 30 is fully inserted in outer elongated member 20. This contact between the portion of intermediate section 34 including through-opening 40 and outer elongated member 20 may help facilitate the compression of intermediate section 34 upon the application of a proximal pulling force on dilator 30.

Through-opening 40 may have any suitable shape. For example, perimeter 41 of through-opening 40 defined by outer wall 35 of dilator 30 and at the outer surface of dilator 30 may have an elongated elliptical shape, as illustrated in FIG. 1. In some examples, through-opening 40 may be extend along a longitudinal axis 48 to a greater or lesser extent than the example of FIG. 1. For example, through-opening 40 can extend from intermediate section 34 longitudinally into proximal section 32 and/or distal section 36. In other examples, through-opening 40 may be radially wider (in a direction orthogonal to longitudinal axis 48) than the example of FIG. 1.

Figure 3:
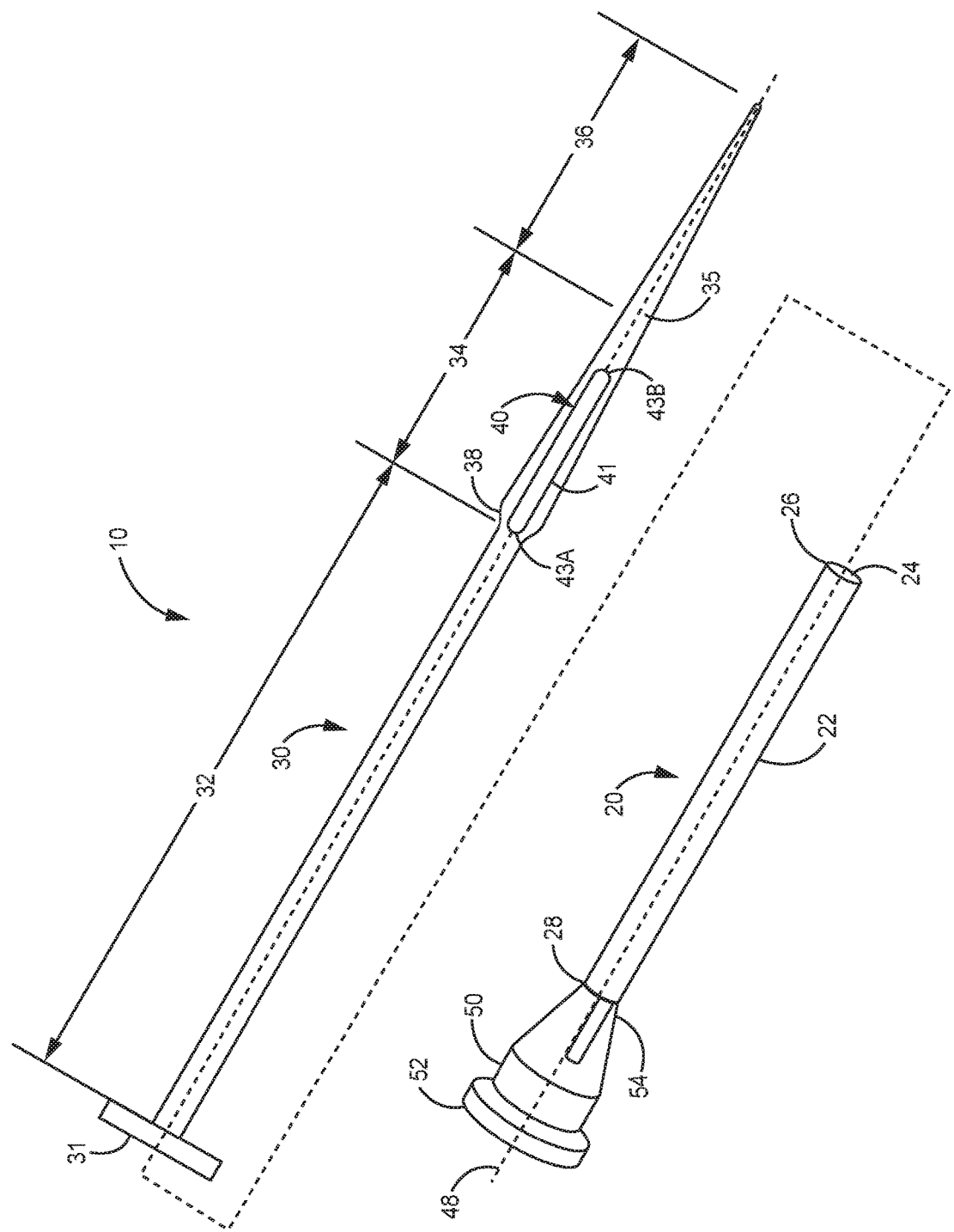
FIG. 3 is an exploded view of the introducer apparatus of FIG. 1.

In another example, perimeter 41 has at least one portion that is sized or shaped differently than another portion of perimeter 41. For example, although perimeter 41 is illustrated in FIG. 3 as having substantially the same dimensions and curvature at proximal end 43A and distal end 34B, in other examples, perimeter 41 may have a different curvature or other geometry at the ends 43A, 43B. For example, a curvature of perimeter 41 at distal end 43B may define a larger arc than an arc defined by perimeter 41 at proximal end 43A, thereby creating an ovoid or semi-ovoid overall shape of perimeter 41. In other examples, a curvature of perimeter 41 at proximal end 43A may define a larger arc than an arc defined by perimeter 41 at distal end 43B. In such examples, the relatively larger arc of perimeter 41 at distal end 43B (or proximal end 43A) may help facilitate the compression of intermediate section 34 in response to pulling of dilator 30 in a proximal direction into inner lumen 40 of outer elongated member 20. The shape of the through-openings described herein are merely illustrative and in other examples, the one or more through-openings defined by intermediate section 34 of dilator 30 may have any suitable shape.

In still other examples, perimeter 41 of through-opening 40 may have other shapes, such as, but not limited to, a rectangular shape, a circular shape, an irregular shape (e.g., a serpentine edge) or any other shape that may be suitable for allowing intermediate section 34 to assume a collapsed configuration when a clinician withdraws dilator 30 proximally into outer elongated member 20.

Through-opening 40 may have any suitable configuration with respect to intermediate section 34 of dilator 30 that enables dilator 30 to be collapsible from an expanded configuration to a collapsed configuration. In some examples, the dimensions of through-opening 40 may vary depending on whether intermediate section 34 of dilator 30 is in the expanded configuration or the collapsed configuration. For example, as described below with respect to FIGS. 2A and 2B, a given dimension of through-opening 40 may be smaller when intermediate section 34 is in the collapsed configuration than when intermediate section 34 is in the expanded configuration. This variability in the dimensions of through-opening 40 may allow dilator 30 to be proximally withdrawn into lumen 24 of outer elongated member 20 when intermediate section 34 is in the collapsed configuration.

Figure 2B:
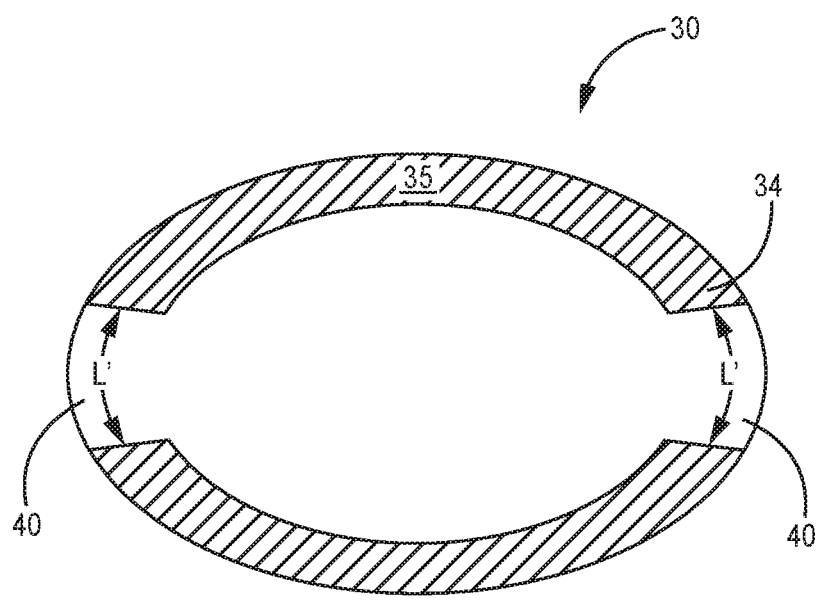
FIG. 2B is a cross-sectional view of the dilator of FIG. 1 in a collapsed configuration, where the cross-section is taken along a plane orthogonal to a longitudinal axis of the dilator.

FIGS. 2A and 2B are cross-sectional illustrations of dilator 30 of FIG. 1, the cross-section taken along line A-A in FIG. 1, which extends orthogonal to longitudinal axis 48 of dilator 30. The perspective provided by the cross-section of FIGS. 2A and 2B faces proximally toward outer elongated member 20 of introducer apparatus 10. However, for illustrative purposes, only dilator 30 is shown in FIGS. 2A and 2B. As shown in FIG. 2A, through-opening 40 extends an arc length L along two arcs of a circle formed by the cross-section of dilator 30 at intermediate section 34 when intermediate section 34 is in the expanded configuration. Thus, in total, through-opening 40 extends a total distance of 2L along the perimeter of the cross-section of intermediate section 34 shown in FIG. 2A. In some examples, the total distance 2L may account for approximately 5% to about 50% of a perimeter of a cross-section of intermediate section 34 (e.g., a circumference in the case of a circular cross-section) when intermediate section 34 is in the expanded configuration. This perimeter of the cross-section of intermediate section 34 may also be referred to as a cross-sectional perimeter. In examples in which dilator 30 tapers, such as in the example described with respect to FIG. 1, the distance 2L may be measured along a circle formed by a cross-section taken at any point of intermediate section 34 that includes through-opening 40.

The cross-sectional perimeter of dilator 30 can be, for example, a circumference in examples in which dilator 30 has a circular cross-section. Dilator 30 may have other shapes in cross-section. In examples in which dilator 30 is not circular in cross-section, a length L of through-opening 40 along a cross-sectional perimeter of dilator 30 may still be measured when dilator 30 is in the expanded configuration, and a distance similar to distance 2L calculated accordingly.

The magnitude of an arc length L (or similar distance) of through-opening 40 may vary depending on whether intermediate section 34 is in an expanded configuration or a compressed configuration. That is, the magnitude of arc length L may be relatively greater when intermediate section 34 is in the expanded configuration compared to when intermediate section 34 is in a compressed configuration. For example, the total distance 2L may extend along approximately 25% to about 50% of the circumference of a circle formed by the cross-section of intermediate section 34 when intermediate section 34 is in the expanded configuration, as shown in FIG. 2A.

As shown in FIG. 2B, through-opening 40 extends an arc length L' along two arcs of a circle formed by the cross-section of dilator 30 at intermediate section 34 when intermediate section 34 is in the compressed configuration. Thus, in total, through-opening 40 extends a total distance of 2L' along the circle formed by the cross-section of intermediate section 34 shown in FIG. 2B. Arc length L' is less than arc length L (FIG. 3A). Thus, a total distance 2L' of through-opening 40 when intermediate section 34 of dilator 30 is compressed may account for less than approximately 25% to about 50% to of the cross-sectional perimeter of the compressed intermediate section 34. As shown in FIG. 2B, intermediate section 34 defines a smaller cross-sectional perimeter in the compressed configuration, thereby reducing the profile of intermediate section 34. The reduction of the cross-sectional perimeter of intermediate section 34 when intermediate section 34 is in the compressed configuration may allow dilator 30 to be proximally withdrawn into lumen 24 of outer elongated member 20 and subsequently removed from apparatus 10 to permit other devices, substances, or the like to be introduced into a patient via lumen 24.

In the examples described above, the dimensions of through-opening 40 may be selected to provide a desired degree of flexibility and compressibility to intermediate section 34. In examples in which a relatively high degree of compressibility of intermediate section 34 is desired, relatively larger dimensions may be chosen for arc length L. In comparison, relatively smaller dimensions may be chosen for arc length L if a relatively low degree of compressibility of intermediate section 34 is desired.

The degree of compressibility required to enable intermediate section 34 to be withdrawn into inner lumen 24 of outer elongated member 20 when dilator 30 is in the collapsed configuration may depend, at least in part, on the expandability of the material or materials from which dilator 30 and outer elongated member 20 are formed. For example, if outer elongated member 20 is formed from a material having relatively high expandability such that lumen 24 is configured to expand radially outward when a pulling force is applied to a proximal portion of dilator 30, then a relatively low degree of compressibility for intermediate section 34 of dilator 30 may be required to accommodate the withdrawal of dilator 30 into lumen 24. In such examples, the dimensions of through-opening 40 may be relatively smaller than in examples in which a relatively high degree of compressibility is required.

In another example, outer elongated member 20 may be formed from a material having relatively low expandability, such that lumen 24 is not configured to substantially expand radially outward when a pulling force is applied to a proximal portion of dilator 30. In such examples, a relatively higher degree of compressibility for intermediate section 34 of dilator 30 may be required to accommodate the withdrawal of dilator 30 into lumen 24. In these examples, the dimensions of through-opening 40 may be relatively larger than examples in which a relatively low degree of compressibility is required.

FIG. 3 is an exploded view of introducer apparatus 10 of FIG. 1, with outer elongated member 20 and dilator 30 illustrated separately. As described above with respect to FIG. 1, outer elongated member 20 includes housing member 50 mechanically or integrally connected to proximal end 28 of outer elongated member 20. In some examples, housing member 50 may be configured to be held in a hand of a clinician. In examples in which housing member 50 is configured to be held in the hand of a clinician, housing member 50 may have a shape that is ergonomically formed to rest within a human hand. In addition, housing member 50 may be configured to have substantial stiffness to resist flexing during use by the clinician, and may be shaped to transmit force (e.g., a proximal withdrawal force, a distal pushing force, or a torqueing force) from the hand of the clinician to elongated member 20 or dilator 30 (when introducer apparatus 10 is assembled).

As described above with respect to FIG. 1, when introducer apparatus 10 is assembled in the insertion configuration, at least a portion of intermediate section 34 extends distally past distal end 26 of outer elongated member 20. At the junction of outer elongated member 20 and the portion of intermediate section 34 that extends distally past distal end 26, outer elongated member 20 and dilator 30 may have complementary sloping or tapered regions. For example, as shown in the example of FIG. 3, a proximal portion of intermediate section 34 defines sloping wall 38, which is tapered radially inward in a proximal direction. In some examples, sloping wall 38 is located along intermediate section 34, such that sloping wall 38 is seated against sloping wall 68 (shown in FIG. 5) of outer elongated member 20 when dilator 30 is fully inserted in outer elongated member 20 in the assembled configuration of introducer apparatus 10. In addition, as described above with respect to FIG. 1, housing member 50 defines a lumen or channel (not shown) extending from proximal end 52 to distal end 54. The channel extending through housing 50 has a dimension in cross-section that is equal to or greater than a cross-sectional dimension of lumen 24 of outer elongated member 20. Thus, dilator 30, or another device which may be inserted or withdrawn through lumen 24, may also pass through the channel of housing 50.

In some examples, introducer apparatus 10 may be provided to the clinician in the assembly configuration illustrated in FIG. 3. In other examples, introducer apparatus 10 may be provided to the clinician in a pre-assembled configuration in which dilator 30 is received within elongated member 20, e.g., as shown in FIG. 3. It may, in some situations, be advantageous to provide introducer apparatus 10 in a pre-assembled configuration, such that the total amount of time needed to perform a medical procedure may be reduced.

Figure 4A:
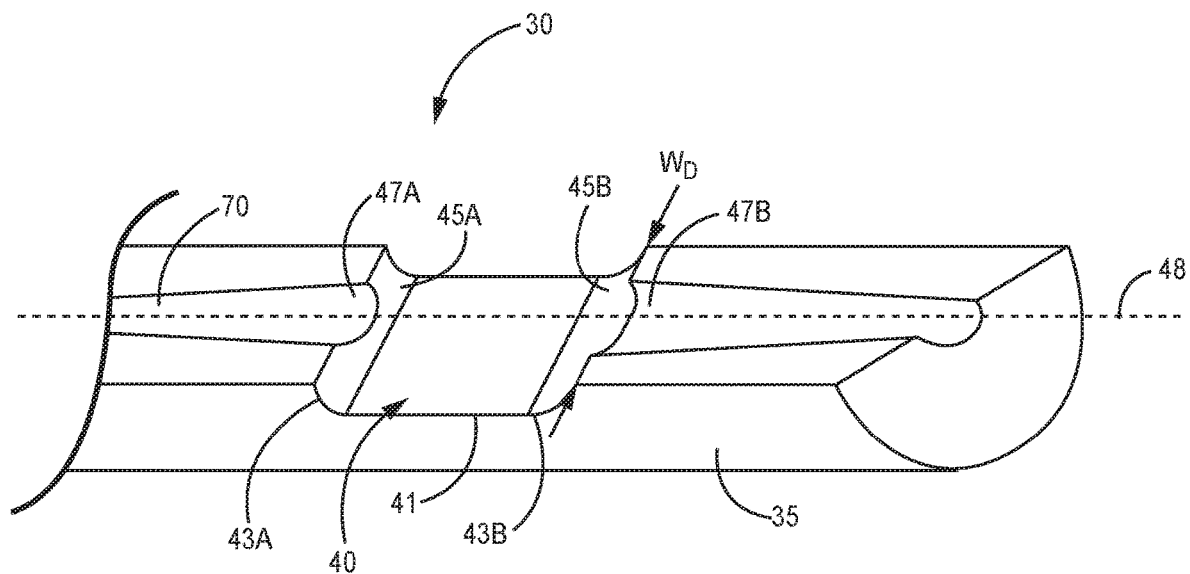
FIG. 4A is a cross-sectional view of an example dilator of the introducer apparatus of FIG. 1, where the cross-section is taken along a longitudinal axis of the dilator.

FIG. 4A is a cross-sectional perspective view of dilator 30 of the introducer apparatus 10 of FIG. 1, where the cross-section is taken along longitudinal axis 48. FIG. 4A illustrates an example configuration of through-opening 40. In the example of FIG. 4A, dilator 30 may be substantially solid except for through-opening 40 and a guidewire lumen 70, which are defined by dilator 30. As shown in FIG. 4A, dilator 30 defines wall portions 45A, 45B of through-opening 40, which may have any suitable dimensions and proportions. Wall portions 45A, 45B extend across width "WD" of dilator 30, as shown in FIG. 4A. In the example of FIG. 4A, the position of through-opening 40 is centered with respect to a central longitudinal axis 48 of introducer apparatus 10. Thus, width WD of dilator 30 shown in FIG. 4A represents a thickest point of dilator 30. Wall portions 45A, 45B respectively define proximal lumen opening 47A and distal lumen opening 47B. Lumen openings 47A, 47B expose guidewire lumen 70 and permit a guidewire or other device to traverse through guidewire lumen 70 and across through-opening 40 from a proximal end to a distal end of dilator 30. Guidewire lumen 70 may extend along a longitudinal axis 48 from proximal section 32 of dilator 30 to distal section 36, and, in some examples, may be centered along a central longitudinal axis 48. Guidewire lumen 70 may have any suitable cross-sectional dimension for tracking over a guidewire used in a medical procedure. In some examples, guidewire lumen 70 may be used in methods for the use of introducer apparatus 10, such as examples in which a clinician employs a guidewire to create an insertion path and track introducer apparatus 10 along the insertion path to a tissue site within the patient.

During use of introducer apparatus 10, a clinician may advance a guidewire or other device distally within lumen 70. Guidewire lumen 70 is bifurcated by through-opening 40, such that when introducer apparatus 10 is tracked over a guidewire, the guidewire exits the portion of lumen 70 proximal to through-opening 40, traverses through-opening 40, and then enters the portion of lumen 70 distal to through-opening 40. After reaching proximal lumen opening 47A, the guidewire or other device may exit lumen 70, traverse across through-opening 40, and re-enter lumen 70 at distal lumen opening 47B. In some examples, lumen 70, through-opening 40, or both, may be configured to facilitate the reintroduction of a guidewire (or other member) through openings 47A, 47B. For example, wall portion 45A may have a surface that tapers radially inward toward proximal lumen opening 47A of lumen 70, and wall portion 45B may have a surface that tapers radially inward toward distal lumen opening 47B of lumen 70. In addition to, or instead of, wall portions 45A, 45B defining the respective tapers, proximal lumen opening 47A may be relatively wide relative to a more proximal part of lumen 70, such that at least a portion of lumen 70 tapers inward in a proximal direction starting from proximal lumen opening 47A, and distal lumen opening 47B may be relatively wide relative to a more distal part of lumen 70, such that at least a portion of lumen 70 tapers radially inward in a distal direction starting from distal lumen opening 47B.

The inwardly-sloping surfaces of wall portions 45A, 45B and/or the tapering portions of lumen 70 at openings 47A, 47B may form a funnel shape. The funnel shape formed by wall portions 45A, 45B and/or lumen openings 47A, 47B may guide facilitate the alignment of a guidewire or other device with the respective lumen opening 47A, 47B after exiting lumen 70 at proximal lumen opening 47A. For example, when a guidewire is being advanced through lumen 70 in a distal direction, the guidewire may exit proximal opening 47B and subsequently contact inwardly sloping surface of distal wall portion 45B and/or distal lumen opening 47B, which may deflect the guidewire distally into lumen 70 as it reaches distal lumen opening 47B. Similarly, when a proximal end of a guidewire is being inserted into lumen 70 in a proximal direction, such that the guidewire first exits distal opening 47B and then enters proximal opening 47A, the inwardly sloping surface of proximal wall portion 45A and/or proximal lumen opening 47A may deflect the guidewire proximally into lumen 70 as it reaches proximal lumen opening 47A.

Figure 4B:
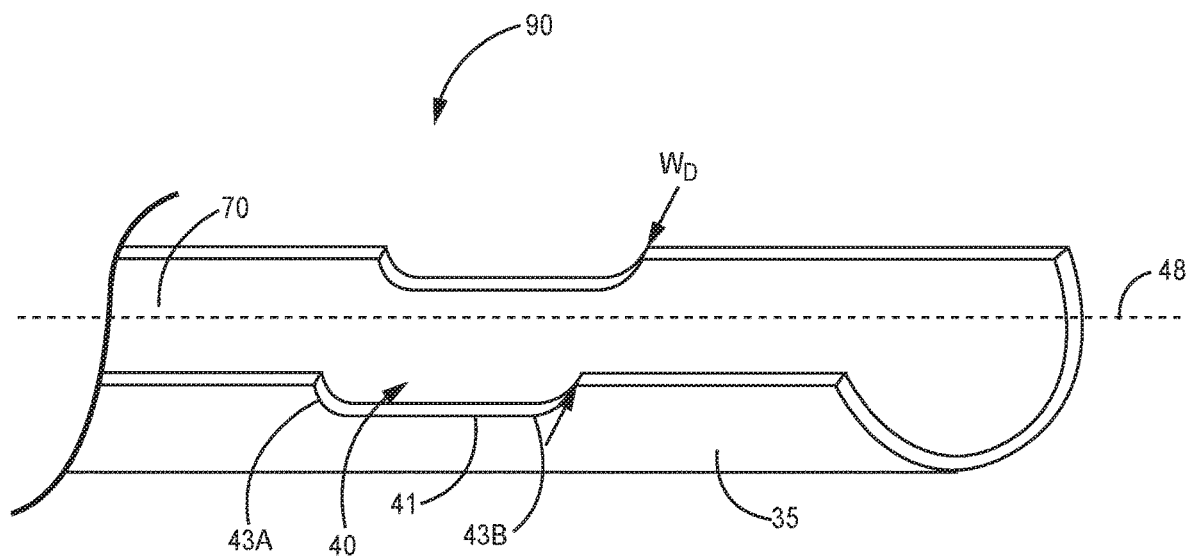
FIG. 4B is a cross-sectional view of another example dilator of the introducer apparatus of FIG. 1, where the cross-section is taken along a longitudinal axis of the dilator.

FIG. 4B is a cross-sectional view of another example dilator 90 of that can be used with introducer apparatus 10. As with FIG. 4A, the position of through-opening 40 of FIG. 4B is centered with respect to longitudinal axis 48. Thus, width WD of dilator 30 shown in FIG. 4B represents a thickest point of dilator 30. The cross-sectional view of dilator 90 of FIG. 4B is taken along a longitudinal axis 48 of introducer apparatus 10, and illustrates another example configuration of through-opening 40. In the example of FIG. 4B, dilator 90 may be substantially hollow. In contrast to dilator 30 shown in FIG. 4A, dilator 90 does not define wall portions 45A, 45B of through-opening 40, such that there is a gap between opposite sides of outer wall 35 of dilator 90. In other examples, dilator 90 may include an inner elongated member, such as inner elongated member 42 illustrated in FIG. 7. As described below with respect to FIG. 7, inner elongated member 42 may define a pathway that bridges a through-opening defined by a dilator such that a portion of inner elongated member 42 is exposed by the through-opening. In such examples of FIG. 4B, inner elongated member 42 may reduce the potential for a guidewire to escape from lumen 70 and protrude through through-opening 40 as dilator 90 is positioned over the guidewire, which may occur during a medical procedure.

Figure 5:
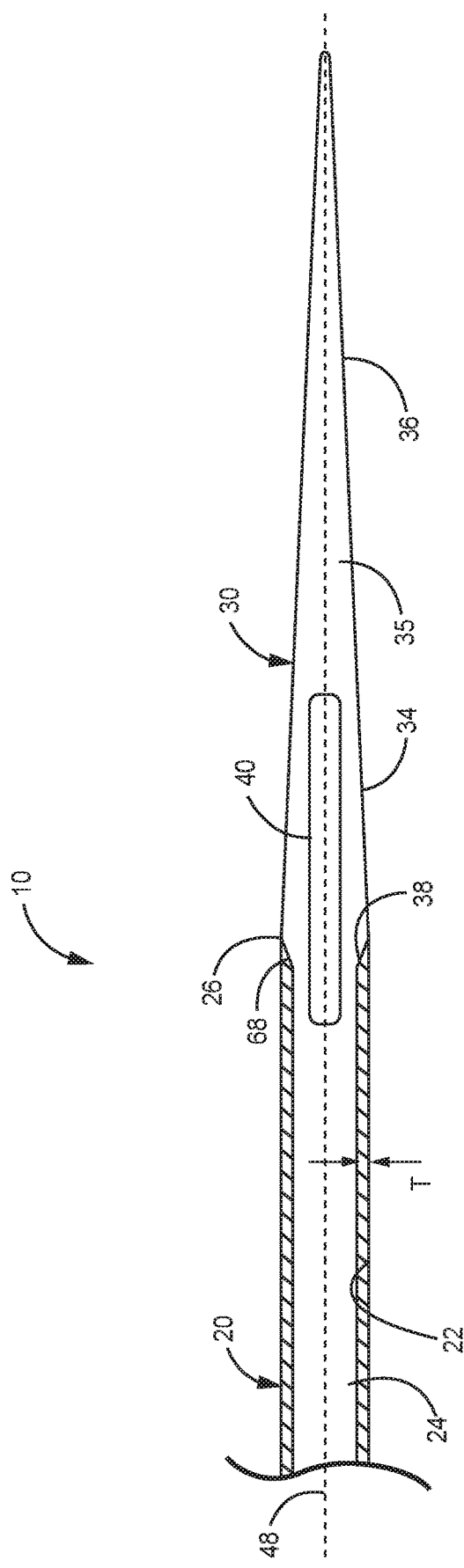
FIG. 5 is a side view of the introducer apparatus of FIG. 1, which illustrates the outer elongated member in cross-section and the dilator received within an inner lumen of the outer elongated member.

FIG. 5 is a side view of a distal portion of introducer apparatus 10 of FIG. 1, which illustrates outer elongated member 20 in cross-section and dilator 30 received within inner lumen 24 of outer elongated member 20. In some examples, as shown in FIG. 5, a proximal portion of through-opening 40 is received within lumen 24 of outer elongated member 20, and a distal portion of through-opening 40 extends distally past distal end 26 of outer elongated member 20. Through-opening 40 configures intermediate section 34 to collapse radially inward as dilator 30 is pulled into lumen 24 by a proximal pulling force is applied to dilator 30.

In some examples, a distal portion of outer elongated member 20 (the distal portion including distal end 26) is configured to facilitate the compression of intermediate section 34 of dilator 30 into a compressed configuration and the subsequent withdrawal of distal section 36 of dilator 30 into inner lumen 24. For example, as shown in the example of FIG. 5, outer wall 22 of outer elongated member 20 may define a proximally tapering lumen (defined by a sloping wall 68), such that inner lumen 24 tapers in a proximal direction from a larger diameter at a distalmost portion of lumen 24 to a smaller diameter at a proximal portion of lumen 24. Outer wall 22 of outer elongated member 20 may have a substantially constant thickness "T," which is measured from an inner surface of wall 22 to an outer surface of wall 22, from proximal end 28 to a location proximal to distal end 26. However, as a result of the proximal tapering of outer wall 22, a portion of wall 22 at distal end 26 of outer elongated member 20 has a thickness that is less than the thickness of the portion of wall 22 proximal to distal end 26. That is, inner lumen 24 of outer elongated member 20 increases in diameter at distal end 26, such that a cross-sectional dimension of lumen 24 at sloping wall 68 is larger than a cross-sectional dimension of lumen 24 proximal to distal end 26.

In addition, in some examples, a proximal portion of intermediate section 34 defines sloping wall 38, which is tapered radially inward in a proximal direction. In some examples, sloping wall 38 is located along intermediate section 34 such that it is seated against sloping wall 68 of outer elongated member 20 when dilator 30 is fully inserted in outer elongated member 20 in the assembled configuration of introducer apparatus 10. When a clinician exerts a proximal pulling force on proximal section 32 of dilator 30, intermediate section 34 experiences an increased resistance to the pulling force along sloping wall 38, where it engages with sloping wall 68 of outer elongated member 20. This increased resistance to the proximal pulling force may be translated into a compressive force that is exerted by sloping wall 68 of outer elongated member 20 onto sloping wall 38 of intermediate section 34. The compressive force acts in a radially inward direction. This compressive force may cause intermediate section 34 to collapse, e.g., cause through-opening 40 to decrease in size as intermediate section 34 assumes a smaller outer diameter. In this way, the engagement between sloping wall 68 of outer elongated member 20 and sloping wall 38 of intermediate section 34 may facilitate compression of intermediate section 34 into the collapsed configuration. The angle of sloping walls 38, 68 (measured relative to longitudinal axis 48) may be substantially similar (e.g., the same or nearly the same) in some examples. This may help increase the compressive force applied to intermediate section 34 by sloping wall 68 of outer elongated member 20 and may, therefore, also decrease the proximal pulling force required to withdraw intermediate section 34 of dilator 30 into inner lumen 24.

In some examples, the internal chamfer (e.g., in an interior surface of outer elongated member 20) resulting from sloping wall 68 may provide less production fallout during manufacturing as compared to an elongated member defining an outer chamfer. While an outer chamfer (e.g., a chamfering of an outer diameter, on an exterior surface of an outer elongated member) may help smooth the transition between the dilator and the outer elongated member, the outer chamfer may be subject to more processing during manufacturing in order to meet visual standards. Visual standards (e.g., standards pertaining to the appearance of a manufactured item) may not be related to the performance or function of introducer apparatus 10, but may add to the complexity of the manufacturing process or create additional waste. In the examples in which outer elongated member 20 includes an inner chamfer resulting from sloping wall 68, visual standards may not be applied, which may result in less potential production fallout than may occur with an outer elongated member defining an outer chamfer.

In the example shown in FIG. 5, intermediate section 34 and outer elongated member 20 are configured to fit together substantially closely, such that dilator 30 occupies inner lumen 24. For example, the cross-sectional dimension of lumen 24 at distal end 26 of outer elongated member 20 may be substantially the same (e.g., the same or nearly the same) as the cross-sectional dimension (e.g., an outer diameter in the case of a circular cross-section) of intermediate section 34 at the proximal end of sloping wall 38 of dilator 30. As an example, if outer elongated member 20 and dilator 30 each have circular cross-sections, then the outer diameter of outer elongated member 20 at distal end 26 may be substantially the same as the outer diameter of intermediate section 34 at the distal end of sloping wall 38 of dilator 30. In this way, an outer surface of introducer apparatus 10 at the junction of outer elongated member 20 and dilator 30 is substantially smooth and free of gaps or ridges. The cross-sections described in this paragraph are taken in a direction orthogonal to longitudinal axis 48.

In other examples, the cross-sectional dimension of lumen 24 at distal end 26 may not be substantially the same as the cross-sectional dimension of intermediate section 34 at the proximal portion of sloping wall 38. For example, depending upon the material from which dilator 30 is made, the cross-sectional dimension of intermediate section 34 at sloping wall 38 may be larger than the cross-sectional dimension of lumen 24 at distal end 26. In such examples, the material of dilator 30 may be selected such that dilator 30 is partially compressible to enable dilator 30 to be received within lumen 24 of outer elongated member 20 without closing off guidewire lumen 70 of dilator 30. The partial compressibility of dilator may enable a smooth outer transition region 60 (shown in FIG. 1) to be defined between outer elongated member 20 and dilator 30 when dilator 30 is received within lumen 34 of outer elongated member 20.

The outer cross-sectional dimensions of outer elongated member 20 and dilator 30 may be selected to provide a smooth outer transition region 60 where dilator 30 and outer elongated member are joined. The cross-sections described in this paragraph are taken in a direction orthogonal to longitudinal axis 48. In its expanded state, the portion of intermediate section 34 that is immediately distal to distal end 26 of outer elongated member 20 when dilator 30 is fully inserted in outer elongated member 20 has a diameter that is greater than a diameter of inner lumen 24, such that the change in diameter between outer elongated member 20 and dilator 30 at region 60 is minimized. For example, the diameter of the portion of intermediate section 34 that is immediately distal to distal end 26 of outer elongated member 20 when dilator 30 is fully inserted in outer elongated member 20 may be substantially equal to (e.g., equal to or nearly equal to) the outer diameter of outer elongated member 20 at distal end 26.

In some examples, outer elongated member 20 may fit over dilator 30 to create an interference fit therebetween. A configuration of introducer apparatus 10 in which an interference fit exists between outer elongated member 20 and dilator 30 may help provide structural stability and torqueability to introducer apparatus 10 during a medical procedure. In some examples, the portion of dilator 30 that is received within lumen 24 when introducer apparatus 10 is in the assembled configuration may have a cross-sectional dimension (in a direction orthogonal to longitudinal axis 48) that is equal to or slightly larger than a cross-sectional dimension of lumen 24. In examples in which a cross-sectional dimension of the portion of dilator 30 that is received within lumen 24 is slightly larger than a cross-sectional dimension of lumen 24, dilator 30 may be formed from a relatively more compressible material, such as a compressible polymer. In such examples, the material from which outer dilator 30 is formed may be selected to permit dilator 30 to compress radially inward when a clinician applies a proximal pulling force to section 32 of dilator 30, thereby allowing dilator 30 to compress into the collapsed configuration and be withdrawn proximally into lumen 24.

The thickness of wall 22 may be selected based on one or more considerations, such as, but not limited to, the desired degree of flexibility of outer elongated member 20, the type of procedure for which introducer apparatus 10 is to be used, or any combination thereof. In some examples, wall 22 may have thickness of approximately 10-40 millimeters (mm). The material of wall 22 also may be selected based on the same or similar considerations. For example, a material having relatively greater flexibility may be selected for applications in which introducer 10 is to be navigated through or around tortuous portions of the anatomy.

Figure 6:
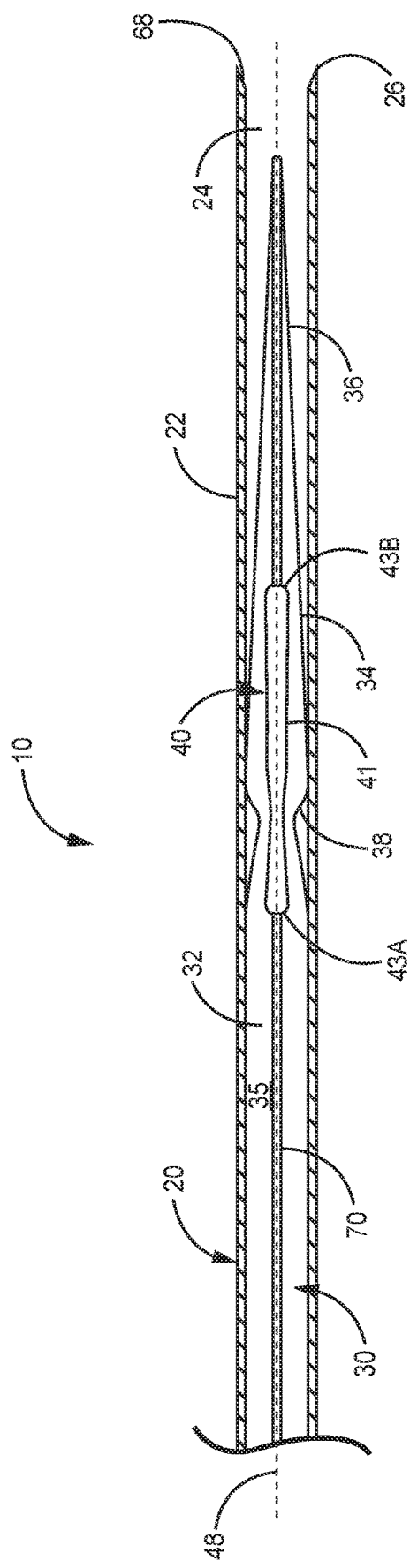
FIG. 6 is a side view of the introducer apparatus of FIG. 1 during withdrawal of the dilator proximally into the lumen of the outer elongated member, and illustrates the intermediate section of the dilator in a collapsed configuration and the outer elongated member in cross-section.

FIG. 6 is a side view of apparatus 10 of FIG. 1 and illustrates an example configuration of dilator 30 when dilator 30 is withdrawn proximally into lumen 24 of outer elongated member 20 (shown in cross-section) and when intermediate section 34 of dilator 30 is in a collapsed configuration. As shown in FIG. 6, when intermediate section 34 of dilator 30 is in a collapsed configuration, at least a portion of the walls of dilator 30 defining through-opening 40 are closer together (compared to when intermediate section 34 is not in a collapsed configuration). As a result, the outer dimension of at least a portion of intermediate section 34 is decreased to be less than or equal to the diameter of lumen 24, which enables intermediate section 34 of dilator 30 to be received within lumen 24 of outer elongated member 20, as shown in FIG. 6.

In some examples, dilator 30 defines guidewire lumen 70, as illustrated in FIG. 6. Guidewire lumen 70 may extend along a longitudinal axis 48 from proximal section 32 to distal section 36, and, in some examples, may be centered along a longitudinal axis 48. In other examples, lumen 70 may not be fully centered along longitudinal axis 48, but may, for example, traverse around through-opening 40. After enlarging an insertion path using introducer apparatus 10, a clinician may withdraw dilator 30 from the patient. For example, the clinician may exert a proximal pulling force on a proximal section 32 of dilator 30, which may extend proximally of housing 50, thereby causing dilator 30 to assume the collapsed configuration shown in FIG. 6. As the clinician continues to exert a proximal pulling force on a proximal portion of dilator 30, dilator 30 moves proximally into lumen 24 of outer elongated member 20 such that intermediate section 34 and distal section 36 of dilator 30 become fully housed within lumen 24, as illustrated in FIG. 6. Dilator 30 then may be proximally withdrawn fully through lumen 24 and removed from introducer apparatus 10. Elongated outer member 20 may be left in place within the insertion path during and after removal of dilator 30 from introducer apparatus 10.

In some examples, dilator 30 may include one or more structures or other elements that may facilitate the introduction of a guidewire through guidewire lumen 70, such as inner elongated member 42 that extends longitudinally across through-hole 40. An inner elongated member may define a pathway for a guidewire (or another guide member) as a clinician advances an introducer apparatus over the guidewire, which may help increase the ease with which the clinician may perform a medical procedure. Inner elongated member 42 may in some examples also reduce the time required for the medical procedure, as less time may be required for the clinician to align the guidewire with a guidewire lumen 70 in a portion of dilator 30 distal to through-opening 40. Additional features and advantages of inner elongated member 42, or a similar element, are discussed below with respect to FIGS. 6 and 7.

Figure 7:
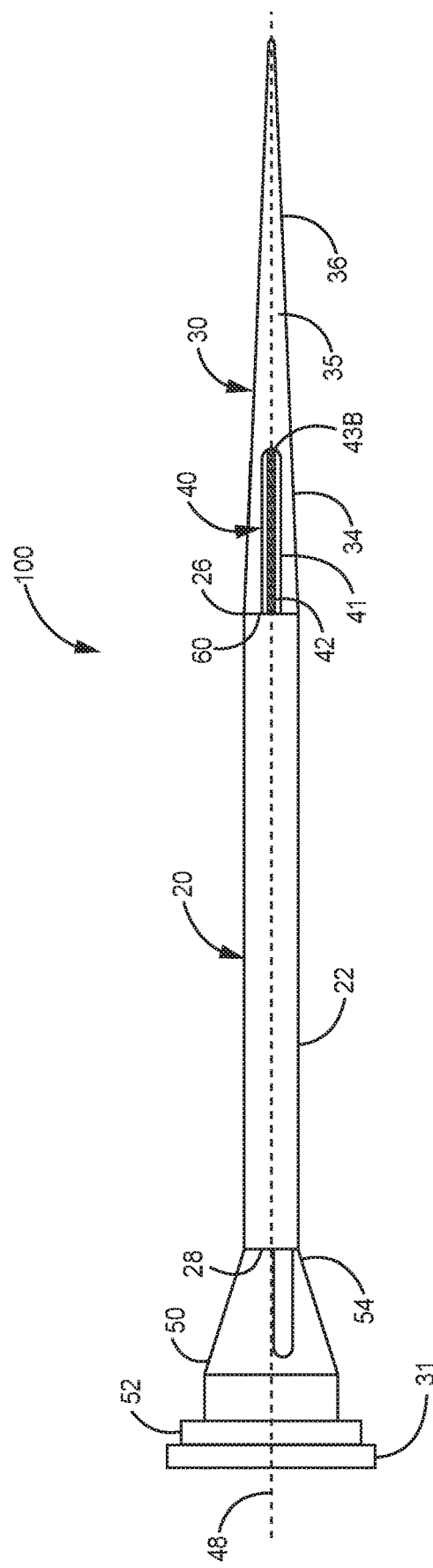
FIG. 7 is a side view of another example introducer apparatus including an outer elongated member, a collapsible dilator received within a lumen of the outer elongated member, and an inner elongated member received within a lumen of the dilator, where an intermediate section of the dilator is in an expanded configuration and extends distally past a distal end of the outer elongated member.

FIG. 7 is a side view of another example introducer apparatus 100. As with introducer apparatus 10 of FIGS. 1-6, introducer apparatus 100 includes outer elongated member 20 and dilator 30 defining through-opening 40 and received within lumen 24 of outer elongated member 20, wherein intermediate section 34 of dilator 32 is illustrated in an expanded configuration and extending distally past distal end 26 of outer elongated member 20. Dilator 30 may include guidewire lumen 70, as described above. Many of the features of introducer apparatus 100 may be substantially similar to the components of introducer apparatus 10 described with respect to FIGS. 1-5, and will not be discussed again in detail here.

In addition, introducer apparatus 100 further includes inner elongated member 42 extending across through-opening 40 and aligns with guidewire lumen 70 of dilator 30. Inner elongated member 42 may be, for example, a tubular structure or another structure that is configured to receive a guidewire.

Inner elongated member 42 may define a pathway that bridges through-opening 40 such that a portion of inner elongated member 42 is exposed by through-opening 40. In such examples, inner elongated member 42 may reduce the potential for a guidewire to escape from lumen 70 and protrude through through-opening 40 as dilator 30 is positioned over the guidewire, which may occur during a medical procedure. In some cases, it may be advantageous to reduce the potential for a guidewire to escape from lumen 70. For example, instances in which a guidewire protrudes through through-opening 40 may require a clinician to make repeated attempts to position apparatus 100 over the guidewire, thereby wasting time, causing unnecessary user frustration, and presenting the potential for damage to the guidewire or components of apparatus 100. Thus, inner elongated member 42 may allow a clinician to perform a medical procedure with greater ease and efficiency.

In some cases, in addition to bridging the gap in inner lumen 70 resulting from through-opening 40, inner elongated member 42 may provide stiffness to portions of introducer apparatus 100. For example, inner elongated member 42 may serve as a reinforcing member for intermediate section 34 of dilator 30. In addition, inner elongated member 42 may provide an advantageous stiffening effect to intermediate section 34 of dilator 30. While a degree of flexibility of dilator 30 may be desired, in some cases it also may be desirable to reinforce the portion of intermediate section 34 in which through-opening 40 is located, thereby preventing intermediate section 34 from becoming overly flexible.

In some examples, inner elongated member 42 may comprise a hypotube formed from a material that may be selected to provide stiffness to a portion of introducer apparatus 100, such as intermediate section 34 of dilator 30, while maintaining the flexibility of outer elongated member 20. Thus, inner elongated member 42 may simultaneously provide advantageous additional stiffness to intermediate section 34 of dilator 30, which may reduce a potential of dilator 30 to kink near through-opening 40, while not impeding a desired degree of flexibility of outer elongated member 20. In examples in which inner elongated member 42 is formed from a material more stiff than outer member 20, dilator 30, or both outer member 20 and dilator 30, the stiffness of inner elongated member 42 may enhance the pushability of apparatus 100 through tissue (e.g., dense or fibrous tissue). Example materials from which inner elongated member 42 may be formed include, but not limited to, one or more of a nickel-titanium alloy (e.g., Nitinol), stainless steel, a polymer, or combinations thereof.

A cross-sectional dimension of inner elongated member 42 may have any dimensions suitable for reception within lumen 70 of dilator 30, without filling the space defined by through-hole 40, such that through-hole 40 still permits intermediate section 34 of dilator 30 to compress in a direction orthogonal to the longitudinal axis 48 (to achieve the compressed configuration), and such that a guidewire may be movably received within inner elongated member 42. That is, a cross-sectional dimension of inner elongated member 42 may be sufficiently small to avoid impeding the desired degree of compressibility of intermediate section 34 of dilator 30, where the cross-section is taken in a direction orthogonal to longitudinal axis 48. In some examples, inner elongated member 42 is sized such that the inner walls of intermediate section 34 that define through-opening 40 contact inner elongated member 42 when intermediate section 34 is in the collapsed configuration. Thus, in some examples, the degree of collapsibility of intermediate section 34 may be limited by the cross-sectional dimension of inner elongated member 42. Thus, the dimensions of inner elongated member 42 may be selected to ensure sufficient collapsibility of intermediate section 34 of dilator 30 to allow intermediate section 34 to be withdrawn proximally into lumen 24 of outer elongated member 20. For example, an outer diameter of inner elongated member 42 may be approximately about 25% or less of an outer diameter of dilator 30.

Inner elongated member 42 may have any suitable length for traversing across through-opening 40. In some examples, inner elongated member 42 is received within guidewire lumen 70, and may extend along the entire length of dilator 30 or only a part of the length of dilator 30. For example, inner elongated member 42 may extend only within intermediate section 34, only within intermediate section 34 and distal section 36, or may extend from within proximal section 32 to a distal end of dilator 30. In other examples, a proximal end of inner elongated member 42 may be connected to a portion of dilator 30 proximal to through-opening 40 and a distal end of inner elongated member 42 may be connected to portion of dilator 30 distal to through-opening.

In examples in which inner elongated member 42 is a structure separate from dilator 30, inner elongated member 42 can be attached to dilator 30 using any suitable technique. In some examples, inner elongated member 42 can be inserted into dilator 30 and mechanically connected thereto, such as by welding, the use of adhesive materials, or any other suitable process. In examples in which inner elongated member 42 and dilator 30 are connected by welding, any suitable welding procedures, such as ultrasonic welding, may be used. In examples in which inner elongated m ember 42 and dilator 30 are connected by an adhesive material, any suitable adhesive material, such as cyanoacrylate, may be used. In some examples, a manufacturing process for dilator 30 of FIG. 7 may include overmolding dilator 30 over inner elongated member 42. The overmolding of dilator 30 over inner elongated member 42 may be advantageous for at least several reasons. For example, manufacturing costs may be lower for an overmolding process than for other manufacturing processes, such as processes in which additional steps must be taken to create an interior channel or lumen within dilator 30.

Figure 8:
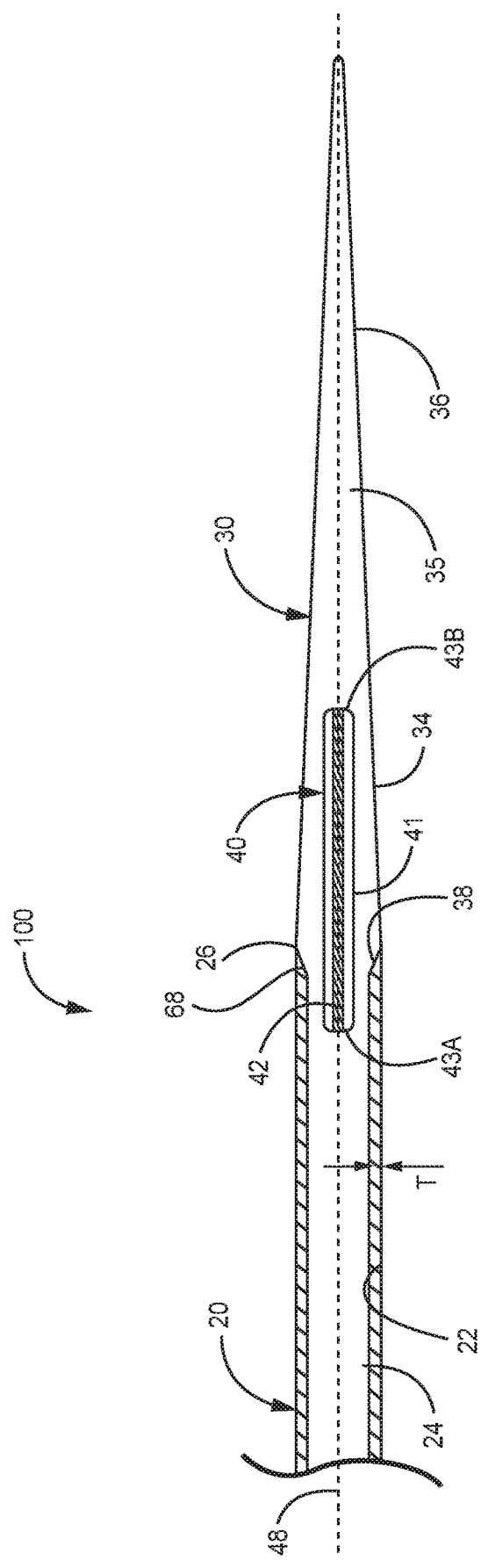
FIG. 8 is a side view of the introducer apparatus of FIG. 7, including the outer elongated member (shown in cross-section), the collapsible dilator having a through-opening received within the outer elongated member, and the inner elongated member received within the lumen of the collapsible dilator.

FIG. 8 is a side view of introducer apparatus 100 of FIG. 7 showing outer elongated member 20 in cross-section and dilator 30 received within inner lumen 24 of outer elongated member 20. As illustrated in FIG. 8, intermediate section 34 of dilator 30 is in the expanded configuration and extends distally past distal end 26 of outer elongated member 20. FIG. 8 further illustrates inner elongated member 42 received within lumen 70 of dilator 30 and extending across through-hole 40.

Although FIGS. 1-8 illustrate dilators that include one through-opening 40, in other examples, a collapsible dilator may include more than one through-opening 40. In the examples illustrated in FIGS. 9 and 10, respective introducer apparatuses 200 and 300 include two through-openings in intermediate section 34 of dilator 30. Although introducer apparatuses 200 and 300 are illustrated as each having two through-openings in intermediate section 34 of dilator 30, more than two through-openings may also be used. In some cases, it may be advantageous to include two or more through-openings in intermediate section 34. For example, the degree and direction of the compressibility of intermediate section 34 may be selected with greater precision than in examples having fewer than two through-openings. In some examples, the number and positioning of the through-openings may be selected to provide the desired level of compressibility while maintaining the desired level of structural integrity of intermediate section 34. In other examples, the number and positioning of the through-openings may be selected to allow intermediate section 34 to have varied compressibility along the longitudinal length thereof. Additional examples, which are not intended to be limiting, are discussed below with respect to FIGS. 9 and 10.

Figure 9:
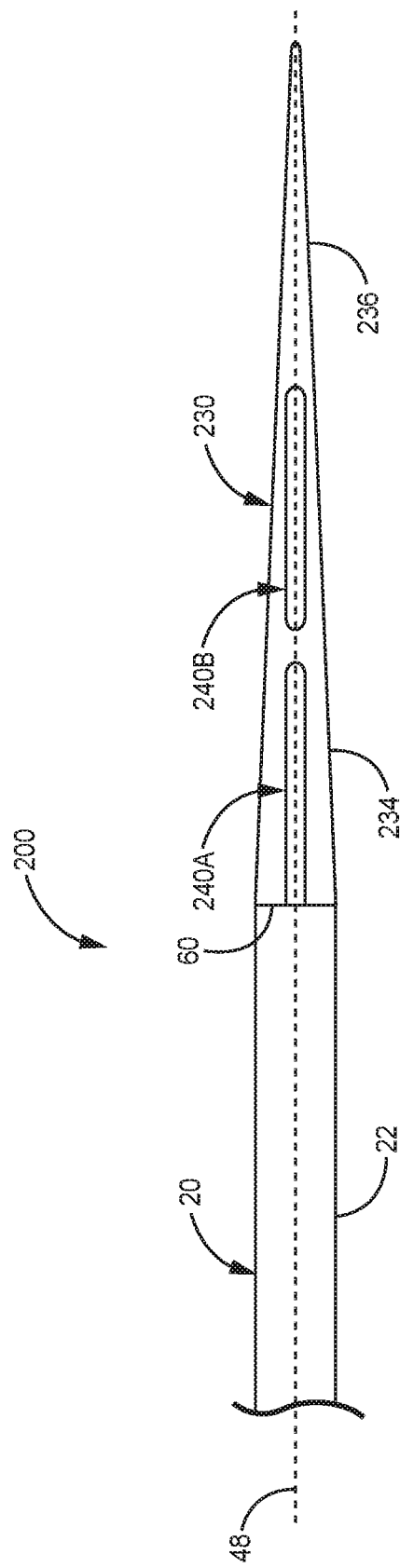
FIG. 9 is a side view of another example introducer apparatus including an outer elongated member and a collapsible dilator defining two or more through-openings centered along a central longitudinal axis of the dilator.

FIG. 9 is a side view of an example introducer apparatus 200, with dilator 230 received within inner lumen 24 of outer elongated member 20. Many of the features of introducer apparatus 200 may be substantially similar to the components of either of introducer apparatus 10 of FIGS. 1-6 or introducer apparatus 100 of FIGS. 7 and 8. For example, intermediate and distal sections 234, 236 of dilator 230 may be similar to intermediate sections 34, 36 of dilator 30 and are not described again with respect to FIG. 9. In the example shown in FIG. 9, dilator 230 defines two through-openings 240A and 240B, which are spatially distinct from each other and separated by a portion of outer wall 238 of dilator 230. In the example shown, through-openings 240A, 240B are centered along a longitudinal axis 48 of dilator 230 and spaced longitudinally from each other at a distance that is substantially less than a longitudinal length of either of through-openings 240A, 240B. However, the placement of through-openings 240A, 240B along or around intermediate section 234 may vary. For example, through-openings 240A, 240B may be positioned closer together or further apart along a longitudinal axis 48 of dilator 230, or may not be aligned along longitudinal axis 48, or any combination thereof In an example, through openings 240A, 240B are positioned on opposite sides of longitudinal axis 48, which may be a central longitudinal axis. For example, in examples in which dilator 230 has a circular cross-section, through-openings 240A, 240B may be circumferentially offset or diametrically opposed. The spacing of through-openings 240A, 240B may depend upon one or more considerations, such as a desired length of compressible intermediate section 234.

In other examples, one or both of through-openings 240A, 240B may have different shapes than those illustrated in FIG. 9. For example, a perimeter of one or both of through-openings 240A, 240B may have a rectangular shape, a circular shape, or any other shape that may be suitable for allowing intermediate section 234 to assume a collapsed configuration when a clinician withdraws dilator 230 proximally into outer elongated member 20. The shape of the through-openings 240A, 240B described herein are merely illustrative and not meant to limit the scope of the invention.

Through-openings 240A, 240B may have any suitable dimensions, and the description of through-opening 40 (FIG. 1) may also apply to each of through-openings 240A, 240B. The dimensions of through-openings 240A, 240B may be selected to provide a desired degree of flexibility and compressibility to intermediate section 234.

In some examples, through-openings 240A, 240B may have the same shape and dimensions. In other examples, through-openings 240A. 240B may differ in shape, dimension, or both. For example, through-opening 240B, which may be distal to through-opening 240A, may have smaller dimensions to account for its placement at a location of dilator 230 having a smaller cross-sectional dimension at the location of through-opening 240A. In this example, each of through-openings 240A, 240B may extend across approximately 5% to about 50% of a total cross-sectional dimension of intermediate section 234 when intermediate section 234 is in the collapsed configuration. While apparatus 200 is illustrated in FIG. 9 as not including inner elongated member 42 (FIG. 7), some examples of apparatus 200 may include inner elongated member 42.

Figure 10:
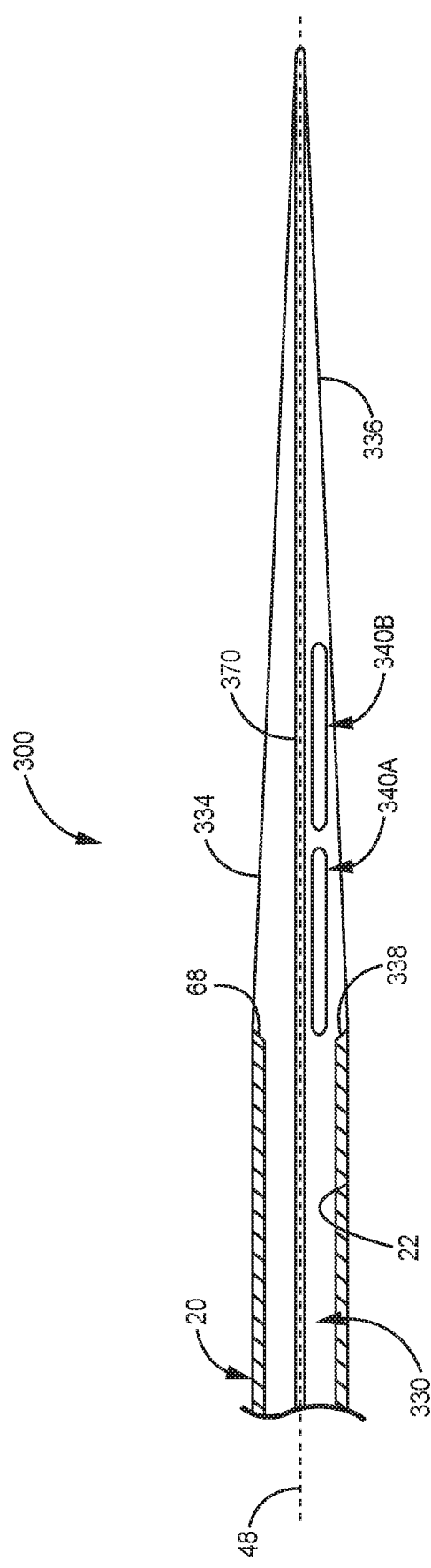
FIG. 10 is a side view of another example introducer apparatus including an outer elongated member (shown in cross-section) and a collapsible dilator defining two or more through-openings that are off-center relative to a central longitudinal axis of the dilator.

FIG. 10 is a side view of introducer apparatus 300, which illustrates outer elongated member 20 in cross-section and dilator 330 received within inner lumen 24 of outer elongated member 20. Many of the features of introducer apparatus 300 may be substantially similar to the components of any of introducer apparatuses 10 of FIGS. 1-6 or introducer apparatus 100 of FIGS. 7 and 8. For example, sloping wall 338 and intermediate and distal sections 334, 336 of dilator 330 may be similar to sloping wall 38 and intermediate sections 34, 36 of dilator 30, respectively, and are not described again with respect to FIG. 10.

As illustrated in FIG. 10, dilator 330 defines two through-openings 340A and 340B. The spacing, dimensions, and shapes of through-openings 340A, 340B may be substantially similar to those described above with respect to through-openings 240A, 240B of FIG. 9. However, in the example of FIG. 10, through-openings 340A, 340B are positioned off-center relative to a longitudinal axis 48 of dilator 330. The shape of the through-openings 340A, 340B described herein are merely illustrative and not meant to limit the scope of the invention.

In some cases, it may be advantageous to position through-openings 340A, 340B off-center relative to a longitudinal axis 48 of dilator 330. For example, as shown in FIG. 10, if guidewire lumen 370 of dilator 30 is centered along longitudinal axis 48, then lumen 370 may not be bisected by through-openings 340A, 340B. In examples of introducer apparatus 300 that do not include inner elongated member 42, such a positioning of through-openings 340A, 340B may help improve the ease and efficiency with which a guidewire may be introduced through guidewire lumen 370, e.g., compared to an example in which a through-opening of dilator 30 exposes the guidewire lumen 370.

In some examples, guidewire lumen 370 of dilator 330 may be centered along a longitudinal axis 48 of dilator 300. However, in other examples, guidewire lumen 370 may be positioned off-center relative to a central longitudinal axis 48 of dilator 300 and/or may not be linear. In these examples, through-openings 340A, 340B may be positioned such that guidewire lumen 370 traverses around through-openings 340A, 340B, and is not exposed by through-openings 340A, 340B. In addition, while apparatus 300 is illustrated in FIG. 10 as not including inner elongated member 42 (FIG. 7), some examples of apparatus 300 may further include inner elongated member 42.

Other arrangements and shapes of through-openings of the example dilators described herein may also be used. In some examples, arrangements and shapes of the through-openings may be selected based on a desired degree of compressibility of the dilator. For example, dilator 330 of FIG. 10 may include one or more additional through-openings (not shown in FIG. 9) on the other side of longitudinal axis 48 from through-openings 340B, 340B. In such examples, the arrangement of through-openings 340A, 340B on opposite sides of a central longitudinal axis 48 may allow for a relatively greater degree of compressibility of intermediate section 34 than other examples in which multiple through-openings are longitudinally spaced from one another along a longitudinal axis of a dilator. As another example, a dilator may define a through-opening having a disc-like shape in cross-section (the cross-section being taken orthogonal to a longitudinal axis), examples of which are described with reference to FIGS. 11A and 11B. In such examples, the disc-like shape of the through-opening may provide uniform compressibility of the dilator about a longitudinal axis of the dilator.

Figure 11A:
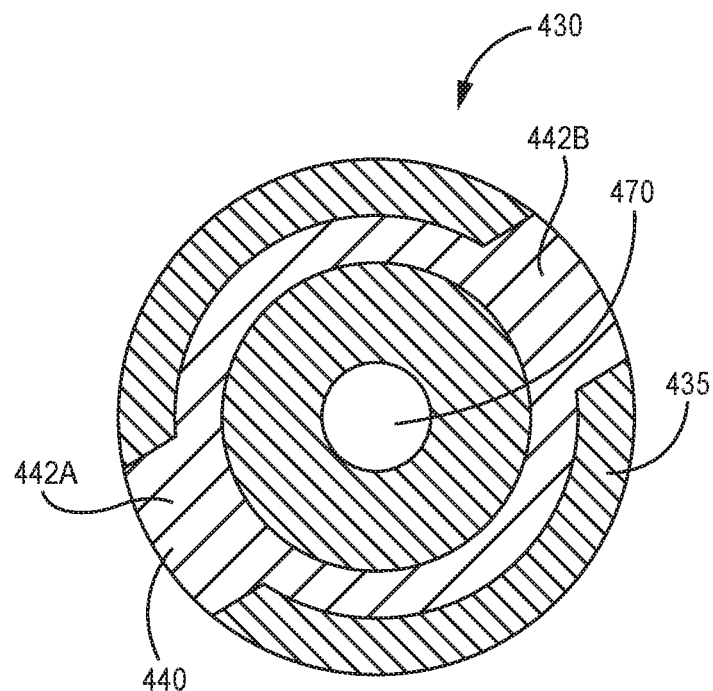
FIG. 11A is a cross-sectional view of an example introducer apparatus that includes a collapsible dilator defining one or more through-openings that extend around a central longitudinal axis of the dilator, where the cross-section is taken orthogonal to the longitudinal axis.

FIG. 11A is a cross-sectional illustration of dilator 430, which is an example of dilator 30 of introducer apparatus 10 of FIG. 1, the cross-section taken along a plane orthogonal to a longitudinal axis of dilator 430 and bisecting through-opening 440. For example, the cross-section shown in FIG. 11A may be a cross-section of an example dilator 30 taken along line A-A in FIG. 1. The longitudinal axis of dilator 430 extends orthogonal to the plane of the image shown in FIG. 11A. Dilator 430 defines through-opening 440, which has a different configuration from the through-openings of the dilators of the other figures. In the example shown in FIG. 11A, through-opening 440 is positioned radially outward from a central longitudinal axis of dilator 430, and does not extend through an entire thickness of dilator 430. Instead, as shown in FIG. 11A, through-opening 440 extends around lumen 470, but does not expose or bisect lumen 470. The configuration of through-opening 440 shown in FIG. 11A provides dilator 430 with a donut-like shape in cross-section, with the center of the donut being define by guidewire lumen 470. A donut-like cross-sectional shape of dilator 430 may provide one or more benefits, such as allowing a guidewire to easily pass through guidewire lumen 470 without becoming radially diverted upon encountering through-opening 440.

Figure 11B:
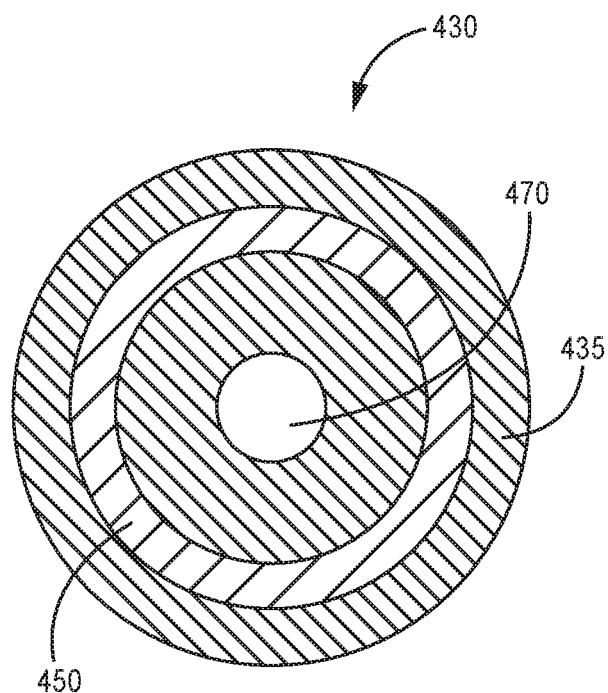
FIG. 11B is a cross-sectional view of another example introducer apparatus that includes a collapsible dilator defining one or more through-openings that extend around a central longitudinal axis of the dilator, where the cross-section is taken orthogonal to the longitudinal axis.

In the example of FIG. 11A, outer wall 435 of dilator 430 defines openings 442A, 442B of through-opening 440, in addition to the portion of through-opening 440 that extends around lumen 470. In other examples, through-opening 440 may define only one of the openings 442A, 442B, or more than two openings 442A, 442B. In other examples of dilator 430, as shown in FIG. 11B, through-opening 450 may not define openings 442A and 442B in wall 435 of dilator 430, such that through-opening 450 extends around lumen 470 but does not extend through outer wall 435 of dilator 430. In any of the examples of FIGS. 11A and 11B, dilator 430 may further include one or more additional through-openings at a position distal or proximal to through-opening 450. In any such examples, the additional through-openings of dilator 430 may have either of the cross-sectional shapes shown in of FIGS. 11A or 11B, or may have another suitable shape.

Figure 12:
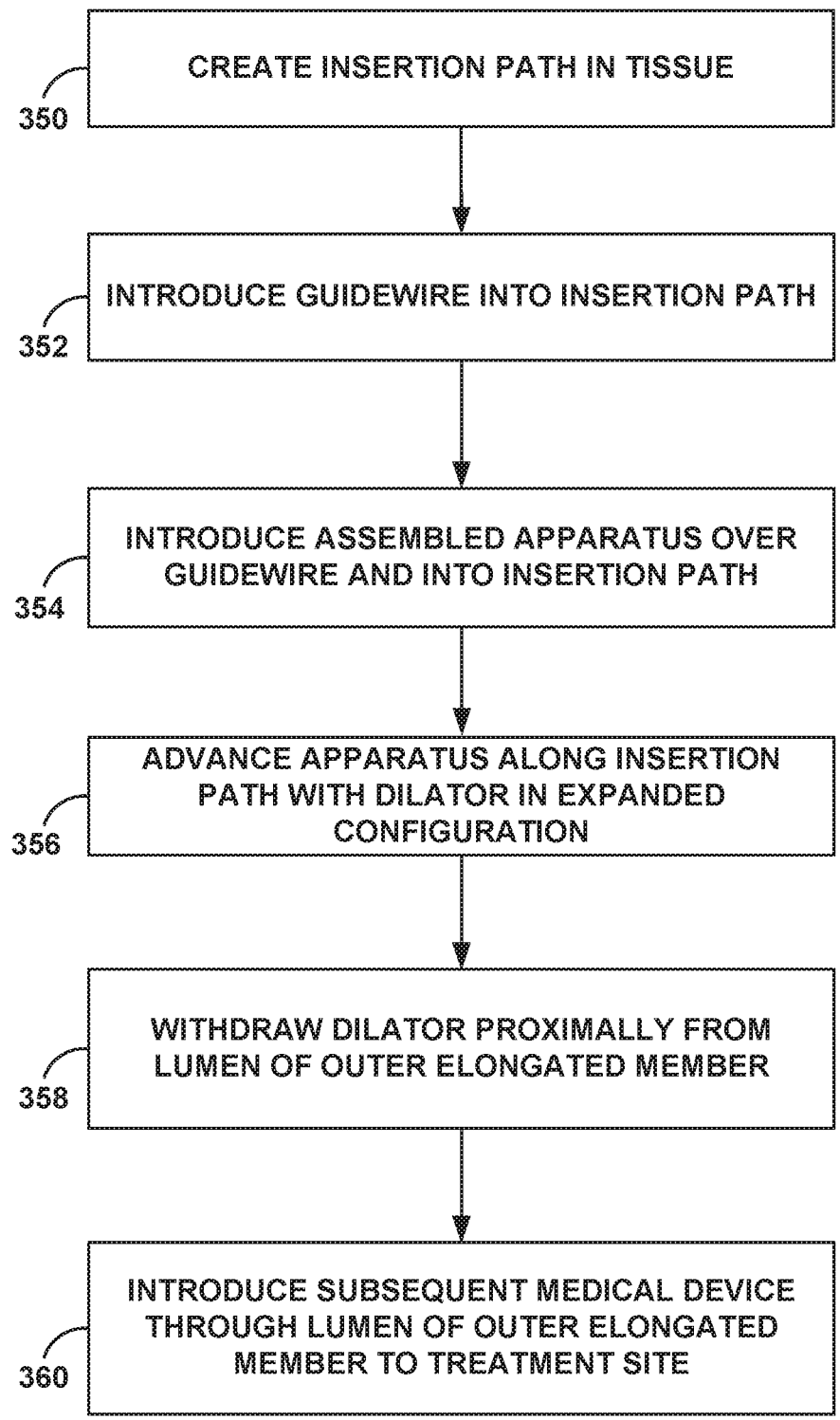
FIG. 12 is a flow diagram illustrating an example method of using the introducer apparatus of any of FIGS. 1-11B.

FIG. 12 is a flow diagram illustrating an example method of using any of apparatuses 10, 100, 200, and 300 of FIGS. 1-11B. While the method shown in FIG. 12 is described with respect to apparatus 10 of FIGS. 1-6, in other examples, the method shown in FIG. 12 can be used with other apparatuses that include a collapsible dilator and an outer elongated member, such as apparatus 100 of FIGS. 7 and 8, apparatus 200 of FIG. 9, or apparatus 300 of FIG. 10.

As shown in FIG. 12, a clinician may create an insertion path from an entry point accessible from outside a patient to a target site within the vasculature, e.g., with the aid of a needle or another device having a cutting surface (350). The clinician may introduce a guidewire into the insertion path, e.g., through the needle or another device (352). Once the insertion path has been created, the clinician may introduce introducer apparatus 10 into the insertion path over the guidewire, with dilator 30 in the expanded configuration and extending past distal end 26 of outer elongated member 20 (354). The clinician then may advance introducer apparatus 10 to the target site within the vasculature of the patient by tracking introducer apparatus 10 along the guidewire within lumen 70, thereby enlarging the insertion path to a size approximately equal to an outer dimension of introducer apparatus 10 (356).

At some point after introducing assembled apparatus 10 into the patient, e.g., after the insertion path has been enlarged, the clinician may withdraw dilator 30 from lumen 24 of outer elongated member 20, leaving outer elongated member 20 in place within the insertion path (358). In some examples, a clinician may grasp housing 50 with one hand while exerting a proximal pulling force on dilator 30, so as to maintain placement of elongated outer member 20 within the insertion path. In some examples, once dilator 10 has been removed from outer elongated member 20, outer elongated member 20 may be used to further aid a medical procedure. As a result of removing dilator 10, for example, one or more medical devices may be introduced into the patient (e.g., into vasculature of the patient) through lumen 24 of elongated outer member 20 (360). As an example, one or more devices such as stents, stimulation leads, and tools for plaque removal, vessel occlusion, blood removal, or fluid introduction may be introduced through elongated member 20, although other devices or substances may be introduced depending upon the medical procedure to be performed.

Thus, by maintaining elongated member 20 within the insertion path during tissue dilation, dilator removal, and subsequent introduction of additional devices, the techniques described herein may provide numerous advantages. For example, the example techniques described herein may save time during a given medical procedure over methods in which an elongated outer member of an introducer apparatus must be removed prior to the introduction of subsequent devices. A reduction in the amount of time needed to perform a given medical procedure may provide one or more benefits, such as increased ease of use, reduced user fatigue, reduced patient discomfort, and an increase in efficiency of the treatment facility, among others.

A collapsible dilator (e.g., dilator 30) may be formed using any suitable manufacturing technique. In some examples, the body of the dilator may be formed by molding, such as by injection molding. As discussed above, in some examples of a dilator that includes inner elongated member 42, dilator 30 may be overmolded around inner elongated member 42 during the manufacturing process. The one or more through-openings can be formed in the dilator using any suitable technique, such as by laser etching or by using a mechanical cutting technique.

Various aspects of the disclosure have been described. These and other aspects are within the scope of the following claims.

What is claimed is:

1. A device comprising:
   an outer elongated member defining a lumen and a first sloping wall; and
   a dilator configured to be received within the lumen of the outer elongated member, the dilator comprising:
   a distal section;
   a proximal section;
   an intermediate section integrally formed with the distal section and the proximal section between the distal section and the proximal section, the intermediate section defining a second sloping wall; wherein, in an assembled configuration of the outer elongated member and the dilator, the second sloping wall is seated against the first sloping wall; and
   a guidewire lumen extending from the proximal section to the distal section, through the proximal, intermediate and distal sections;
   wherein the intermediate section defines a through-opening that configures the intermediate section to be collapsible from an expanded configuration to a collapsed configuration; wherein, the dilator is configured such that as the intermediate section transitions from the collapsed configuration to the expanded configuration, only the intermediate section of the dilator expands in diameter; further wherein the guidewire lumen is bifurcated by the through-opening.

2. The device of claim 1, wherein the distal section includes a distal end of the dilator, the intermediate section being disposed between the proximal section and the distal section; wherein the distal section of the dilator is tapered toward the distal end of the dilator.

3. The device of claim 1, wherein in the collapsed configuration, the intermediate section has a first dilator dimension measured in a direction orthogonal to a longitudinal axis of the dilator, and in the expanded configuration, the intermediate section has a second dilator dimension measured in the direction, the second dilator dimension being greater than the first dilator dimension.

4. The device of claim 3, wherein the through-opening extends along about 5% to about 50% of a perimeter of a cross-section of the dilator taken orthogonal to a longitudinal axis of the dilator.

5. The device of claim 1, wherein the through-opening comprises two or more through-openings.

6. The device of claim 4, wherein at least two of the two or more through-openings are positioned on opposite sides of a central longitudinal axis of the dilator.

7. The device of claim 4, wherein the two or more through-openings are longitudinally spaced from one another relative to a longitudinal axis of the dilator.

8. The device of claim 1, wherein the through-opening is centered along a central longitudinal axis of the dilator.

9. The device of claim 1, wherein the through-opening is off-center relative from a central longitudinal axis of the dilator.

10. The device of claim 1, wherein the through-opening bisects the dilator lumen into a first portion and a second portion, the device further comprising an inner elongated member extending between the first and second portions of the dilator lumen.

11. The device of claim 10, wherein the inner elongated member is exposed by the through-opening.

12. The device of claim 10, wherein the dilator is overmolded around the inner elongated member.

13. The device of claim 1, wherein a perimeter of the through-opening defined by an outer wall of the dilator has a proximal end and a distal end;
   wherein a curvature of the perimeter at the proximal end differs from a curvature of the perimeter at the distal end.

14. The device of claim 13, the perimeter at the distal end has a greater curvature as compared to the perimeter at the proximal end.

15. The device of claim 1, wherein the dilator defines proximal and distal wall portions of the through-opening, wherein the proximal and distal wall portions each define sloping surfaces.

16. The device of claim 1, wherein, in the expanded configuration at least a portion of the intermediate section has a diameter greater than a greatest outer diameter of both of the distal section and the proximal section.

17. An apparatus comprising:
   an outer elongated member defining a lumen extending therethrough, the lumen having a lumen dimension in cross-section; and
   a dilator configured to be received within the lumen of the outer elongated member, the dilator comprising:
   a proximal section;
   a distal section;
   an intermediate section integrally formed with the distal section and the proximal section between the distal section and the proximal section; and
   a guidewire lumen extending from the proximal section to the distal section, through the proximal, intermediate and distal sections; and
   wherein the intermediate section defines a through-opening that configures the intermediate section to be collapsible from an expanded configuration to a collapsed configuration, wherein in the collapsed configuration, the intermediate section has a dilator dimension in cross-section that is less than or equal to the lumen dimension; wherein, the dilator is configured such that as the intermediate section transitions from the collapsed configuration to the expanded configuration, only the intermediate section of the dilator expands in diameter;
   further wherein the guidewire lumen is bifurcated by the through-opening; wherein, in an assembled configuration of the outer elongated member and the dilator, the outer elongated member and dilator abut to collectively define a substantially continuous outer diameter.

18. The apparatus of claim 17, wherein the distal section includes a distal end of the dilator, the intermediate section being disposed between the proximal section and the distal section, wherein the distal section of the dilator is tapered toward a distal end of the dilator; wherein when the proximal section of the dilator is positioned in the lumen of the outer elongated member and the intermediate section is in the expanded configuration, the intermediate section and the distal section extend distally past a distal end of the outer elongated member.

19. The apparatus of claim 17, wherein the through-opening bisects the guidewire lumen into a first portion and a second portion, the apparatus further comprising an inner elongated member extending between the first and second portions of the guidewire lumen.

20. The apparatus of claim 17, wherein when the proximal section of the dilator is positioned in the lumen of the outer elongated member and the intermediate section is in the expanded configuration and extends distally past a distal end of the outer elongated member, the outer elongated member and the intermediate section have substantially same outer dimensions.

21. The apparatus of claim 17, wherein the dilator dimension is substantially equal to the lumen dimension.

22. The apparatus of claim 17, wherein the dilator dimension is a first dilator dimension, and wherein in the expanded configuration, the intermediate section has a second dilator dimension in cross-section, the second dilator dimension being substantially equal to the lumen dimension.

23. The apparatus of claim 17, wherein the dilator dimension is a first dilator dimension, and wherein in the expanded configuration, the intermediate section has a second dilator dimension in cross-section, the second dilator dimension being greater than the lumen dimension.

24. The apparatus of claim 17, wherein the dilator dimension is a first dilator dimension, and wherein in the expanded configuration, the intermediate section has a second dilator dimension in cross-section, the second dilator dimension being greater than an outer dimension of the outer elongated member.

25. The apparatus of claim 17, wherein the dilator dimension is a first dilator dimension, and wherein in the expanded configuration, the intermediate section has a second dilator dimension in cross-section, the second dilator dimension being substantially equal to an outer dimension of the outer elongated member.

26. The apparatus of claim 17, wherein the through-opening comprises two or more through-openings.

27. The apparatus of claim 17, wherein the outer elongated member defines a substantially continuous outer diameter.

28. The apparatus of claim 17, wherein the dilator defines proximal and distal wall portions of the through-opening, wherein the proximal and distal wall portions each define sloping surfaces.

29. The apparatus of claim 17, wherein a perimeter of the through-opening defined by an outer wall of the dilator has a proximal end and a distal end;
wherein a curvature of the perimeter at the proximal end differs from a curvature of the perimeter at the distal end.

30. The device of claim 17, wherein, in the expanded configuration at least a portion of the intermediate section has a diameter greater than the lumen dimension.

\* \* \* \* \*